(12) United States Patent
Dhanijala et al.

(10) Patent No.: US 8,301,396 B1
(45) Date of Patent: Oct. 30, 2012

(54) MINIATURE ULTRAFINE PARTICLE SENSOR

(75) Inventors: Suresh Dhanijala, Potsdam, NY (US); Manish Ranjan, Potsdam, NY (US)

(73) Assignee: Clarkson University, Potsdam, NY (US)

( * ) Notice: Subject to any disclaimer, the term of this patent is extended or adjusted under 35 U.S.C. 154(b) by 255 days.

(21) Appl. No.: 11/975,772

(22) Filed: Oct. 22, 2007

Related U.S. Application Data

(60) Provisional application No. 60/853,623, filed on Oct. 20, 2006, provisional application No. 60/877,142, filed on Dec. 23, 2006.

(51) Int. Cl.
*G01N 31/00* (2006.01)
(52) U.S. Cl. ........................................................ 702/24
(58) Field of Classification Search .................... 702/24, 702/19, 182–188
See application file for complete search history.

(56) References Cited

U.S. PATENT DOCUMENTS 7,298,486 B2 * 11/2007 Wang et al. .................. 356/438

* cited by examiner

*Primary Examiner* — Edward Raymond
(74) *Attorney, Agent, or Firm* — Gerow D. Brill

(57) ABSTRACT

Theory and design of a new electrical-mobility based instrument for measurement of aerosol particle size distributions in real time is presented. Miniature Electrical Aerosol Spectrometer has a rectangular cross-section with two main regions: the Electrostatic Precipitator (ESP) and Classifier sections. The ESP section enables charged particle injection into the classifier section in a narrow range of streamlines at the desired location. The injected charged particles are then segregated based on their electrical mobility in the classifier section and collected on a series of plates that are connected to electrometers. Real-time particle size distribution measurements can be inferred from the electrometer signal strengths with the knowledge of the instrument transfer function. A theoretical approach is developed to calculate Miniature Electrical Aerosol Spectrometer transfer function considering the non-uniformity in the electric and flow fields inside the instrument, and accounting for the instrument dimensions and its operating conditions. The theoretical predictions of size classification characteristics are seen to compare well with numerical results. The modeling results suggest that an optimal operational domain exists for Miniature Electrical Aerosol Spectrometer.

32 Claims, 25 Drawing Sheets

MINIATURE ULTRAFINE PARTICLE SENSOR

CROSS REFERENCE TO RELATED APPLICATIONS

This application is related to provisional applications Ser. No. 60/853,623 filed on Oct. 20, 2006 entitled Compact Electrical Aerosol Spectrometer, and Ser. No. 60/877,142 filed on Dec. 23, 2006 entitled Miniature Ultrafine Particle Sensor are both hereby incorporated by reference.

FIELD OF THE INVENTION

The invention relates to the field of aerosol spectrometers and in particular to electrical-mobility spectrometers and a miniature ultrafine particle sensor.

BACKGROUND OF THE INVENTION

The role of ultrafine particles (UFPs) from a human health perspective is increasingly being recognized (See Ibald-Mulli et al., 2002; and Oberdorster and Utell, 2002, both hereby incorporated herein by reference.), and the interaction of these particles with their environment is dependent on, among other parameters, their size and number concentration (See Penttinen et al. 2001; and Kreyling et al. 2002, both hereby incorporated by reference). Size distribution measurements of ultrafine particles can be made using commercially available scanning electrical mobility spectrometers (SEMS). See Wang and Flagan, 1990, hereby incorporated herein by reference; e.g., TSI scanning mobility particle spectrometer, MSP WPS, and GRIMM DMPS). The scanning electrical mobility spectrometers technique uses a differential mobility analyzer (DMA) (See Kuntson and Whitby, 1975, hereby incorporated herein by reference.) to classify particles based on their electrical mobility and the concentration of the classified particles is, typically measured using a condensation particle counter (CPC). See Agarwal and Sem, 1980, hereby incorporated herein by reference. In the scanning electrical mobility spectrometer instruments, the voltage required for particle classification is exponentially varied to obtain size distributions in a relatively short time (~5 minutes). Faster size distribution measurements are possible by combining the electrical-mobility classification technique with an electrometer detector array. See Matisen, et al., 1992; Mirme, 1994; Tammet et al., 2002; and Biskos et al., 2005, all hereby incorporated herein by reference. Commercial instruments based on this technique include the FMPS (TSI Inc.) and DMS500 (Cambustion Inc.). The availability of these instruments has made ambient ultrafine particles measurements possible in near real-time and at high size resolution.

Accurate estimation of human health effect of ultrafine particles requires size distribution measurements considering their spatial and temporal variability. See Buzorius, et al., 1999; Shi, et al., 2001; and Zhu, et al., 2002, all hereby incorporated herein by reference. Such measurements require the deployment of instruments over a large number of sites or on a mobile platform, but the large cost, size, and power requirements of the existing instruments make such deployments difficult. Existing portable instruments such as the TSI 3007 CPC and the combination ion-optical sensor (See Litton, et al., 2004, hereby incorporated herein by reference) provide a measure of ultrafine number concentration, but no sizing information. For real-time, size-resolved ultrafine particles measurements applicable for large spatial-scale or personal exposure studies, there is a need for a new family of instruments.

BRIEF DESCRIPTION OF THE DRAWINGS

These and other features, aspects, and advantages of the present invention will become better understood with regard to the following description, appended claims, and accompanying drawings where:

SUMMARY OF THE INVENTION

Figure 1:
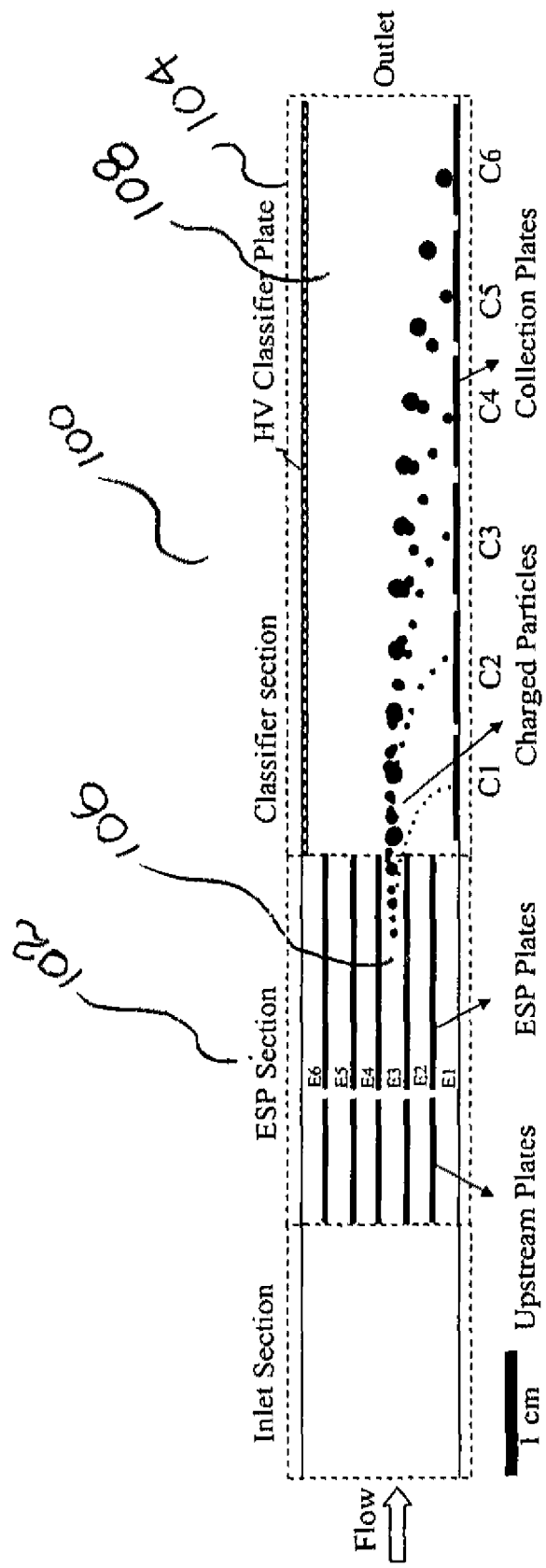
FIG. 1 illustrates a schematic diagram of the Miniature Electrical Aerosol Spectrometer.

The theory and design of a new electrical-mobility based instrument for measurement of aerosol particle size distributions in real time is presented here. A Miniature Electrical Aerosol Spectrometer has a rectangular cross-section with two main regions: the Electrostatic Precipitator (ESP) and Classifier sections. The electrostatic precipitator section enables charged particle injection into the classifier section in a narrow range of streamlines at the desired location. The injected charged particles are then segregated based on their electrical mobility in the classifier section and collected on a series of plates that are connected to electrometers. Real-time particle size distribution measurements can be inferred from the electrometer signal strengths with the knowledge of the instrument transfer function. A theoretical approach is developed to calculate The Miniature Electrical Aerosol Spectrometer transfer function considering the non-uniformity in the electric and flow fields inside the instrument, and accounting for the instrument dimensions and its operating conditions. The theoretical predictions of size classification characteristics are seen to compare well with numerical results. The modeling results suggest that an optimal operational domain exists for Miniature Electrical Aerosol Spectrometer.

The concepts of a Miniature Electrical Aerosol are also demonstrated in a Miniature Ultrafine Particle Sensor with a single collection plate resulting in an electrometer response that is particle size independent. Therefore the net signal from the collection plate is a true measure of the total ultrafine particle number concentration The concepts of a Miniature Electrical Aerosol are demonstrated in a Miniature Ultrafine Particle Sensor with a single collection plate resulting in an electrometer response that is particle size independent. Therefore the net signal from the collection plate is a true measure of the total ultrafine particle number concentration.

A miniature electrical-mobility aerosol spectrometer has: an inlet section; an electrostatic precipitator section; a classifier section; an outlet. The spectrometer further includes a plurality of upstream plates within the electrostatic precipitator section and a plurality of electrostatic precipitator plates within the precipitator section.

The spectrometer further includes a high voltage classifier plate and one or more collection plates within the classifier section.

The spectrometer has a transfer function that determines an optimum configuration of the electrostatic precipitator section and the classifier section. The transfer function includes a series of calculations to account for certain non-linear characteristics of an electric field generated within the spectrometer. The non-uniform electric potential distribution (V) in the spectrometer satisfies $\nabla^2 V = 0$. Individual electric potential contributions of the electrostatic precipitator plates and classifier plates in the classifier section are summed due to the linearity of $$
\begin{array}{c}
\boxed{\begin{array}{c} V_c \\ V_e \rightarrow \\ V_e \rightarrow \end{array} V(x,y) \, 0V \\ 0V \end{array}}
=
\boxed{\begin{array}{c} V_c \quad [A] \\ 0V \, V^C(x,y) \, 0V \\ 0V \end{array}}
+
\sum_{i=1}^{N_e} \boxed{\begin{array}{c} 0V \\ 0V \rightarrow \\ V_e \rightarrow V^{Ei}(x,y) \, 0V \\ 0V \rightarrow \\ 0V \quad [B] \end{array}}
$$
Equation (1)

individual electric potential contributions of the electrostatic precipitator plates are obtained from $$V^C(x,y) = \sum_{n=1}^{\infty} A_n \sin\left(\frac{n\pi x}{L}\right) \sinh\left(\frac{n\pi y}{L}\right)$$
$$\text{where } A_n = \frac{2V_c}{n\pi} \frac{1}{\sinh\left(\frac{n\pi H}{L}\right)} [1-(-1)^n]$$

Equation 2 individual electrical potential contributions of the classifier plates are obtained from $$V^{Ei}(x,y) = \sum_{n=1}^{\infty} B_n \sin\left(\frac{n\pi y}{H}\right)\left(\exp\left(\frac{n\pi}{H}x\right) - \exp\left(\frac{n\pi}{H}(2L-x)\right)\right)$$
where
$$B_n = \frac{2V_e}{n\pi} \frac{1}{\left(1-\exp\left(2L\frac{n\pi}{H}\right)\right)} \left[\cos\left(\frac{n\pi h_u^{i-1}}{H}\right) - \cos\left(\frac{n\pi h_l^i}{H}\right)\right]$$

Equation 3 equation 1 is solved using separation of variables method;

a net electrical potential $$V(x,y) = V^C(x,y) + \sum_{i=1}^{N_e} V^{Ei}(x,y)$$

Equation 4 is obtained by summing individual contributions wherein a net electric field within the spectrometer is a gradient of electric potential.

A closed form of a net flow profile is obtained by combining the individual velocity profiles through the electrostatic channels using a set of Heaviside step functions with a main classifier section velocity profile $$u^E(x, y) = \sum_{i=1}^{Ne+1} \frac{6u_{avg}^E}{(h_u^i - h_l^i)^2}(y - h_l^i)(h_u^i - y)[U(y - h_l^i) - U(y - h_u^i)][U - (-x + p(h_l^i - h_u^{i-1}))];$$ (Equation 1)

$$u^C(x, y) = \frac{6U_{avg}^C}{H^2} y(H - y)U(x - p(h_l^i - h_u^{i-1}));$$ Equation (2)

where $u^C(x,y)$ is the velocity in the classifier section away from the electrostatic precipitator-based flow region, and $U_{avg}^C$ is the average velocity through same classifier section, wherein the Equations 1 and 2 are summed to obtain the velocity field [$u_{net}(x,y)$] in the spectrometer classifier section.

The velocities from Equations 1 and 2 can be used to calculate the stream function $\Psi$ as $$\psi(x,y) = \int^{x,y}[u_x dy - u_y dx];$$

and where $u_x$ and $u_y$, are the x and y velocity components.

The electric flux function, $\phi$ can be calculated as, $$\phi(x,y) = \int^{x,y}[E_x dy - E_y dx],$$

where $E_x$, and $E_y$ are the x and y components of the electric field.

A particle trajectory in the classifier section is obtained by plotting contours of $\Gamma = \psi + Z_p\phi = $ constant where electrical mobility, $Z_p$ is the particle migration velocity in a unit electric field and is given as:

$$Z_p = \frac{neC_c}{3\pi\mu d}$$

where n is an elementary unit of charge, e is the charge on an electron, $C_c$ is a Cunningham Correction factor, $\mu$ is the viscosity of the fluid, and d is the diameter of the particle.

A numerical program is used to obtain equiflow contour paths of particle trajectories of a selected diameter or an electrical mobility from the injection channel through the classifier section and further wherein a fraction of contour lines starting at the injection channel that reach a particular collection plate are calculated. The numerical program is repeated for a range of particle diameters and to obtain particle capture probability or instrument transfer function as a function of particle diameter or electrical mobility for a selected collection plate.

In order to account for particle transmission efficiency in the electrostatic precipitator section, the electrostatic precipitator section is simulated as a rectangular channel with a boundary condition for the electric potential at an interface of the electrostatic precipitator section and the classifier section are obtained from a numerical solution of integrated classifier and electrostatic precipitator sections and further wherein $\nabla^2 V = 0$ is used to obtain a closed form solution of the electric potential distribution inside the channels.

A parabolic velocity profile is used to calculate the stream function for the flow in the electrostatic precipitator channel and further wherein the numerical program is repeated for various particle diameters to get a particle penetration through the channel as a function of particle diameter. The diameter dependent particle penetration is accounted for in a collection characteristics curve in the spectrometer to obtain the transfer function for any flow rate and classifier plate voltage.

The transfer function is used with an inversion subroutine to calculate a particle size distribution entering the spectrometer.

The miniature ultrafine particle sensor includes: an inlet section; an electrostatic precipitator section; a classifier section; a screen; a pump and flow control; an outlet; a high voltage source; a voltage recorder and wireless transmitter; and a module for external communication. A plurality of upstream plates within the electrostatic precipitator section and a plurality of electrostatic precipitator plates are within the precipitator section. A high voltage classifier plate and a single collection plate are within the classifier section. Appropriately selecting the shape of the collection plate can result in a sensor response that has predetermined particle size dependence.

The calculations used in the spectrometer discussed above are included in the sensor design. In addition a final electrometer signal for the signal depends on the transfer function, a size dependent particle charging ratio, and the collection ratio as in $$E = \sum_{n=1}^{\infty} neQ \int_0^{\infty} Nf_n \Omega A_c^* d\log D_p$$

where e is coulomb charge, Q is the flow rate through the sensor, and Dp is a particle diameter. The collection plate area, f(x) varying along a length of the plate, an optimum shape provides a required collection curve is calculated using $$\kappa = neQf_n\Omega \left( \frac{\int_{x_{Z_p}^{min}}^{x_{Z_p}^{max}} f(x)\,dx}{w\int_{x_{Z_p}^{min}}^{x_{Z_p}^{max}} dx} \right)$$

where $x^{min}_{Z_p}$ and $x^{max}_{Z_p}$ represent positions along the flow direction (x) between which particles of mobility $Z_p$ are captured and f(x) represents the collection plate width as a function of length along the flow wherein a total collection plate area is, $$A_c^* = \int_0^L f(x)\,dx$$

A first order approach to the collection plate area shape function is to assume that a particle beam width through the electrostatic precipitator injection channel is negligibly small so that f(x) will be constant between $x^{min}_{Z_p}$ and $x^{max}_{Z_p}$ as in $$f(x) = \frac{\kappa w}{neQf_n\Omega} \qquad (7)$$

The collection plate curve with a shape as given by f(x) provides an electrometer signal that has a predetermined dependence on particle size.

The measurement of particles methods with a predetermined dependence are used as an ultrafine total concentration sensor having a collection curve independent of particle size and provides a signal proportional to the total concentration of particles smaller than 100 nm.

An ultrafine lung-response sensor using these techniques has a size dependence collection curve and provides a signal that is directly related to the number concentration of particles likely to be deposited in a lung.

DETAILED DESCRIPTION OF THE INVENTION

A new instrument, called the Miniature Electrical Aerosol Spectrometer (MEAS), for real-time ultrafine particle size distribution measurements is described herein. The salient features of the Miniature Electrical Aerosol Spectrometer instrument include: compact size, fast response, single-flow operation, and a design that will enable eventual miniaturization. A comprehensive theoretical approach is outlined to determine Miniature Electrical Aerosol Spectrometer sizing characteristics. The instrument performance is obtained as a function of its physical dimensions and operating conditions. A theoretical analysis suggests that the Miniature Electrical Aerosol Spectrometer can be designed to have an optimal operating condition different from typical electrical-mobility instruments.

Miniature Electrical Aerosol Spectrometer Design:

A Miniature Electrical Aerosol Spectrometer 100 has a rectangular cross-section with two primary regions: the electrostatic precipitator section 102 (ESP) and the classifier section 104 as illustrated in FIG. 1. Particles will be charged upstream of the Miniature Electrical Aerosol Spectrometer in a bipolar diffusion charger and then sampled into the Miniature Electrical Aerosol Spectrometer 100. In the Miniature Electrical Aerosol Spectrometer 100, the sampled particles first pass through the electrostatic precipitator region 102. This region consists of a set of parallel plates (E1-E6 as illustrated in FIG. 1) that act as electrostatic precipitators when a potential difference is applied across them. The different plates can be individually maintained at different voltage potentials. The parameters of the electrostatic precipitator section, i.e., number of plates, plate spacing, length, and channel potential difference, are chosen such that charged particles with highest electrical mobility can be electrostatically precipitated through the desired channels. Across one selected electrostatic precipitator channel, called the injection channel 106, a zero potential difference is maintained to permit the passage of charged particles into a narrow flow region in the classifier section. The minimum length of the electrostatic precipitator channel plates is determined by the flow velocity, the available potential difference, and the largest particle mobility to be captured. The smallest spacing between the channels is determined by the breakdown voltage for the operating environmental conditions. The flow through of the non-injection electrostatic precipitator channels acts as sheath flow in the classifier section.

In the classifier section, 104 a potential difference is maintained to segregate the injected particles by their electrical mobility. This section consists of a classifier plate 108 maintained at high voltage and a set of collection plates connected to the electrometers (not shown). Charged particles condense out of the flow and are trapped on the collection plates C1-C6 as illustrated in FIG. 1. The uncharged particles entering through the different electrostatic precipitator channels will exit the classifier section 104 unaffected by the applied electric field. Electrometers (not shown) connected to the collection plates will output current signals proportional to the number of charged particles trapped on the plates. For real-time particle size distribution measurement, an array of electrometers are deployed along the length of the flow. The particle sizing characteristics of the Miniature Electrical Aerosol Spectrometer 100 depends on the choice of the injection channel, dimensions of the classifier section 104, voltage on the classifier plate, number of injection channels and collection plates, and average flow velocity. An optimal design of the Miniature Electrical Aerosol Spectrometer 100 requires theoretical understanding of particle behavior in the instrument as a function of its physical dimensions and operating environment.

Theory:

The Miniature Electrical Aerosol Spectrometer 100 sizing performance is characterized by its transfer function. The Miniature Electrical Aerosol Spectrometer transfer function ($\Omega_i^j$) is defined as the probability that a charged aerosol particle of mobility $Z_P$ entering through the injection channel (Ei) reaches the $j^{th}$ collection plate (Cj). Here, we determine the instrument transfer function for non-diffusive particles using the approach of Knutson and Whitby (1975a), hereby incorporated herein by reference.

Figure 2:
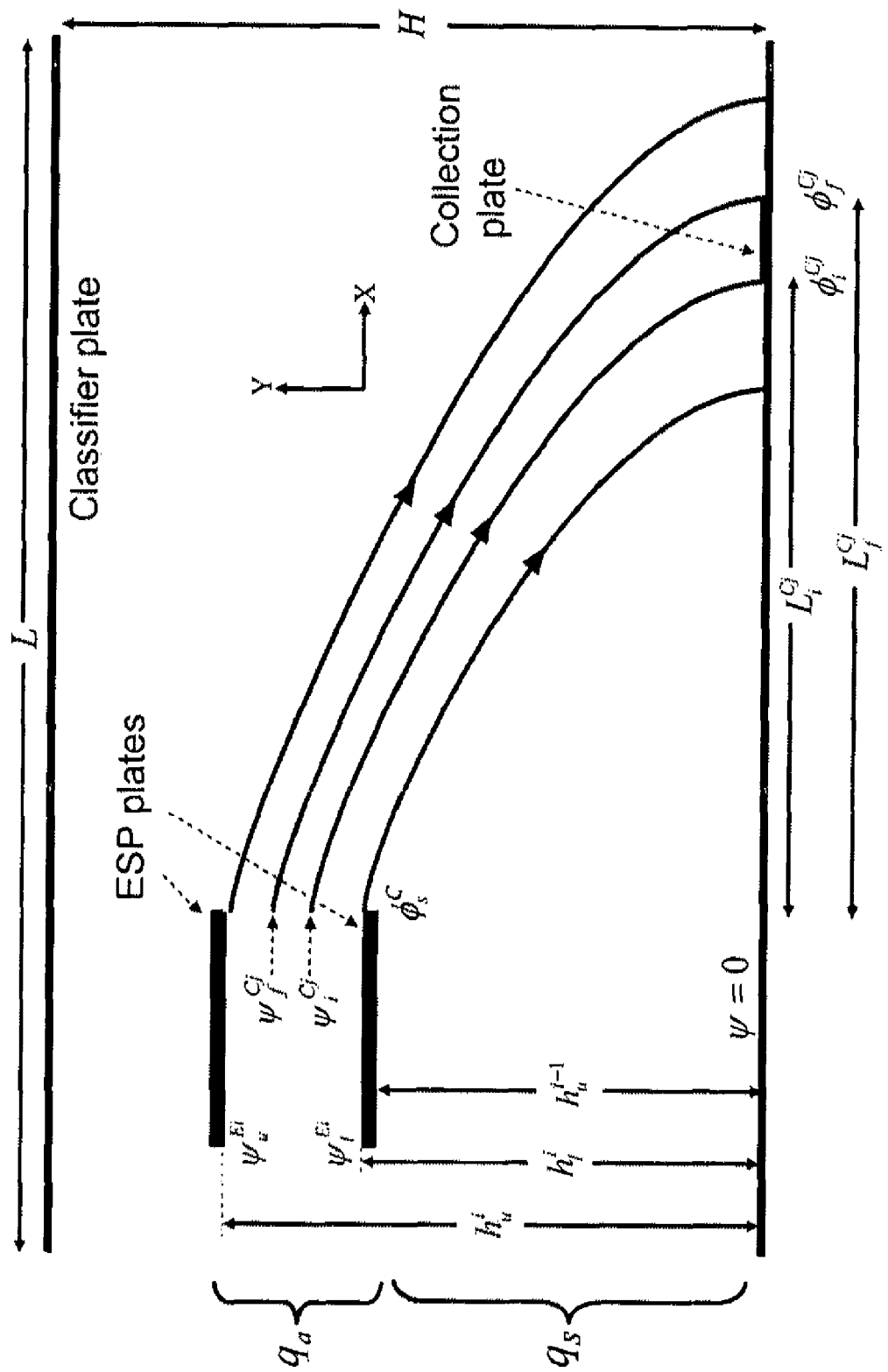
FIG. 2 illustrates a schematic representation of the particle trajectories in the Miniature Electrical Aerosol Spectrometer.

Under the influence of applied electric and drag force, particles move such that:

$$\psi + Z_p \phi = \text{constant} \quad (1)$$

where $\psi$ is the fluid stream function, $\phi$ is the electric flux function and $Z_p$ is the electrical mobility of the particles. As illustrated in FIG. 2, a fraction of particles injected through the injection channel Ei, are captured on the collection plate Cj. For uniform particle concentration in the electrostatic precipitator injection channel, the transfer function ($\Omega_i^j$) can be represented as the fraction of the flow rate through electrostatic precipitator injection channel, Ei, from which particle are collected on Cj. Thus, $$\Omega_i^j = \frac{f(\psi_f^{Cj}) - f(\psi_i^{Cj})}{(\psi_u^{Ei} - \psi_l^{Ei})} \quad (2)$$

where $\psi_l^{Ei}$ and $\psi_u^{Ei}$ are stream function values at the lower and upper ends of the injection channel Ei, and their difference represents the total aerosol flow through the injection channel. The difference in flow stream functions, $f(\psi_f^{Cj}) - f(\psi_i^{Cj})$, determines the flow from where charged particles are captured on the collection plate, Cj, as illustrated in FIG. 2, where the functions, $f(\psi_i^{Cj})$ and $f(\psi_f^{Cj})$ are defined as:

$$f(\psi_i^{Cj}) = \min[\max(\psi_l^{Ei}, \psi_i^{Cj}), (\psi_u^{Ei})]$$

$$f(\psi_f^{Cj}) = \min[\max(\psi_l^{Ei}, \psi_f^{Cj}), (\psi_u^{Ei})] \quad (3)$$

The variables $\psi_i^{Cj}$ and $\psi_f^{Ci}$, are the stream function values at the exit of the electrostatic precipitator section corresponding to the flow streamlines from where particles are just captured at the leading and trailing edges of the collection plate Cj, as illustrated in FIG. 2. The functions $f(\psi_i^{Cj})$ and $f(\psi_f^{Cj})$ bound the stream functions values to the limits of the injection channel. The possible capture scenarios for particles of different mobilities entering the classifier section are listed in Table 1.

TABLE 1

The different possible cases to get the theoretical transfer function of the Miniature Electrical Aerosol Spectrometer.

| Scenario | $f(\psi_i^{Cj})$ | $f(\psi_f^{Cj})$ | $\Omega$ |
|---|---|---|---|
| 1 Particles through ESP injection Ei are captured beyond the collection plate Cj | $\psi_l^{Ei}$ | $\psi_l^{Ei}$ | 0 |

TABLE 1-continued

The different possible cases to get the theoretical transfer function of the Miniature Electrical Aerosol Spectrometer.

| Scenario | $f(\psi_i^{Cj})$ | $f(\psi_f^{Cj})$ | $\Omega$ |
|---|---|---|---|
| 2 Lowermost particle trajectory through ESP injection Ei meets the collection plate Cj while the uppermost particle trajectory is captured beyond Cj | $\psi_l^{Ei}$ | $\psi_f^{Cj}$ | $\dfrac{(\psi_f^{Cj} - \psi_l^{Ei})}{(\psi_u^{Ei} - \psi_l^{Ei})}$ |
| 3 Lowermost particle trajectory through Ei is captured before Cj while the uppermost particle is captured beyond Cj | $\psi_i^{Cj}$ | $\psi_f^{Cj}$ | $\dfrac{(\psi_f^{Cj} - \psi_i^{Cj})}{(\psi_u^{Ei} - \psi_l^{Ei})}$ |
| 4 Particles through ESP injection channel Ei are completely captured on the collection plate Cj | $\psi_l^{Ei}$ | $\psi_u^{Ei}$ | 1 |
| 5 Lowermost particle is captured before Cj while the uppermost particle is captured on Cj | $\psi_i^{Cj}$ | $\psi_u^{Ei}$ | $\dfrac{(\psi_u^{Ei} - \psi_i^{Cj})}{(\psi_u^{Ei} - \psi_l^{Ei})}$ |
| 6 Particles through ESP injection Ei are captured before the collection plate Cj | $\psi_u^{Ei}$ | $\psi_u^{Ei}$ | 0 |

Stream functions $\psi_i^{Cj}$ and $\psi_f^{Cj}$ can be calculated using Eq. (1) from the stream function values at the leading and trailing edge of the collection plate, Cj, and the electric flux function values at the collection plate location ($\phi_i^{Cj}$, $\phi_f^{Cj}$) and the exit of the electrostatic precipitator section ($\phi_s^C$). In a uniform electric field, the electric flux function is independent of height and, hence, is the same for the lower and upper limits of the particle trajectory at the electrostatic precipitator exit. By combining all the cases in Table 1, the general form of Miniature Electrical Aerosol Spectrometer transfer function for the injection channel Ei and collection plate Cj for uniform electric field is given as:

$$\Omega_i^j = \max\left[0, \min\left(1, \frac{Z_p(\phi_f^{Cj} - \phi_i^{Cj})}{\psi_u^{Ei} - \psi_l^{Ei}}, \frac{Z_p(\phi_f^{Cj} - \phi_s^C) - \psi_l^{Ei}}{\psi_u^{Ei} - \psi_l^{Ei}}, \frac{\psi_u^{Ei} - Z_p(\phi_i^{Cj} - \phi_s^C)}{\psi_u^{Ei} - \psi_l^{Ei}}\right)\right] \quad (4)$$

where it is assumed that $\Psi = 0$ along the surface of the collection plates. The transfer function can be further simplified considering the equations for flow and electric fields in the classifier section.

Parabolic Flow Profile and Uniform Electric Field:

For uniform electric field in the 2D classifier region, the electric flux function (0) can be written as:

$$\phi = \frac{\Delta V}{H} x \quad (5)$$

Using Eq. (5), the instrument transfer function (Eq. 4) for uniform electric field can be expressed in terms of the instrument parameters as:

$$\Omega = \left(\frac{1}{q_n}\right) \max\left\{0, \min\left[q_a, V_{te}A_c,\right.\right. \quad (6)$$

$$\left.\left.\left(\frac{q_a + wZ_p(\phi_f^{Cj} - \phi_i^{Cj})}{2} \pm \left(\frac{q_a + 2q_s - wZ_p(\phi_i^{Cj} + \phi_f^{Cj})}{2}\right)\right)\right]\right\}$$

where $\phi_f^{Cj}(=\Delta V/HL_f^{Cj})$ and $\phi_i^{Cj}(=\Delta V/HL_i^{Cj})$ are the electric flux function values in the classifier section at the leading and trailing edges of the collection plate respectively, $L_i^{Cj}$ and $L_f^{Cj}$ are the lengths from the electrostatic precipitator exit to the leading and trailing edges of the collection plate, respectively, w is the width of the classifier section, $q_n$ is the aerosol flowrate through the injection channel, $q_s$ is the sheath flowrate between the aerosol injection channel and the collection plates, and $V_{te}$ is the particle terminal electrostatic velocity. For particles with mobilities that result in maximal capture efficiency, the transfer function height is the minimum of $$\left(1, \frac{V_{te}A_c}{q_a}\right).$$

The transfer function heights for collected particles with mobilities smaller and larger than those with peak efficiency are obtained by subtracting and summing, respectively, the two terms inside the parenthesis in Eq. (6).

For a uniform electric field, the Miniature Electrical Aerosol Spectrometer transfer function resolution ($\Re$; Zhang & Flagan, 1996, hereby incorporated herein by reference), defined as the ratio of the mobility corresponding to the peak in the transfer function ($Z_p^*$) to the full width of the transfer function at one half of the maximum value ($\Delta Z_{(1/2)}$), can be calculated as:

$$\Re = \frac{Z_p^*}{\Delta Z_{(1/2)}} = \left\{ \frac{\dfrac{A_f^{Cj}}{A_i^{Cj}} + \dfrac{q_s + q_a}{q_s}}{\left(\left(\dfrac{A_f^{Cj}}{A_i^{Cj}}\right)\dfrac{q_s + q_a}{q_s} - 1 + \left|\dfrac{q_s + q_a}{q_s} - \dfrac{A_f^{Cj}}{A_i^{Cj}}\right|\right)} \right\} \quad (7)$$

where $A_f^{Cj}(=w L_f^{Cj})$ and $A_i^{Cj}(=w L_i^{Cj})$ are the areas in the classifier section from the electrostatic precipitator exit to the leading and trailing edge of the collection plate respectively. The Miniature Electrical Aerosol Spectrometer transfer function is similar to that of other electrometer-based spectrometers (e.g., DMS instrument; Biskos et. al., 2005) and slightly different from that obtained by Knutson and Whitby (1975) due to the presence of only three flows in the Miniature Electrical Aerosol Spectrometer compared to four flows in the differential mobility analyzer.

As a validation, the theoretical transfer functions derived using the closed form solution are compared with the numerical transfer functions obtained from computational fluid dynamics (CFD) simulations using the software FLUENT® (FLUENT Inc., NH). Flow fields were simulated in FLUENT® considering laminar, incompressible flow, with uniform velocity as the entrance boundary condition. The electric potential distribution in Miniature Electrical Aerosol Spectrometer was calculated in FLUENT® using the user defined scalar (UDS) option. For boundary conditions, the electrostatic precipitator and high voltage classifier plates were set to the desired electric potential values and the entrance and exit boundaries were set to zero potential flux. The electric fields in a Miniature Electrical Aerosol Spectrometer are calculated using an external user defined function (UDF) code in FLUENT®. The user defined function code also calculated the resultant electrical force on the particles in x- and y-directions. The numerical transfer function is calculated from particle trajectory simulations by determining the fraction of particles starting at the Miniature Electrical Aerosol Spectrometer inlet that are trapped on the individual collection plates. For this calculation, trajectories of 300 particles of different diameters are tracked with a time step of 0.5 ms. Based on our initial particle trajectory calculations, it was decided that a set of upstream plates (FIG. 1) at ground potential were required to ensure that charged particles entered the different electrostatic precipitator channels at uniform concentration, independent of the electrostatic precipitator plate voltages. With the upstream plates, the number of particles passing through the electrostatic precipitator injection channel into the classifier section are obtained by just dividing the total number of particles entering Miniature Electrical Aerosol Spectrometer by the number of electrostatic precipitator channels.

Figure 3:
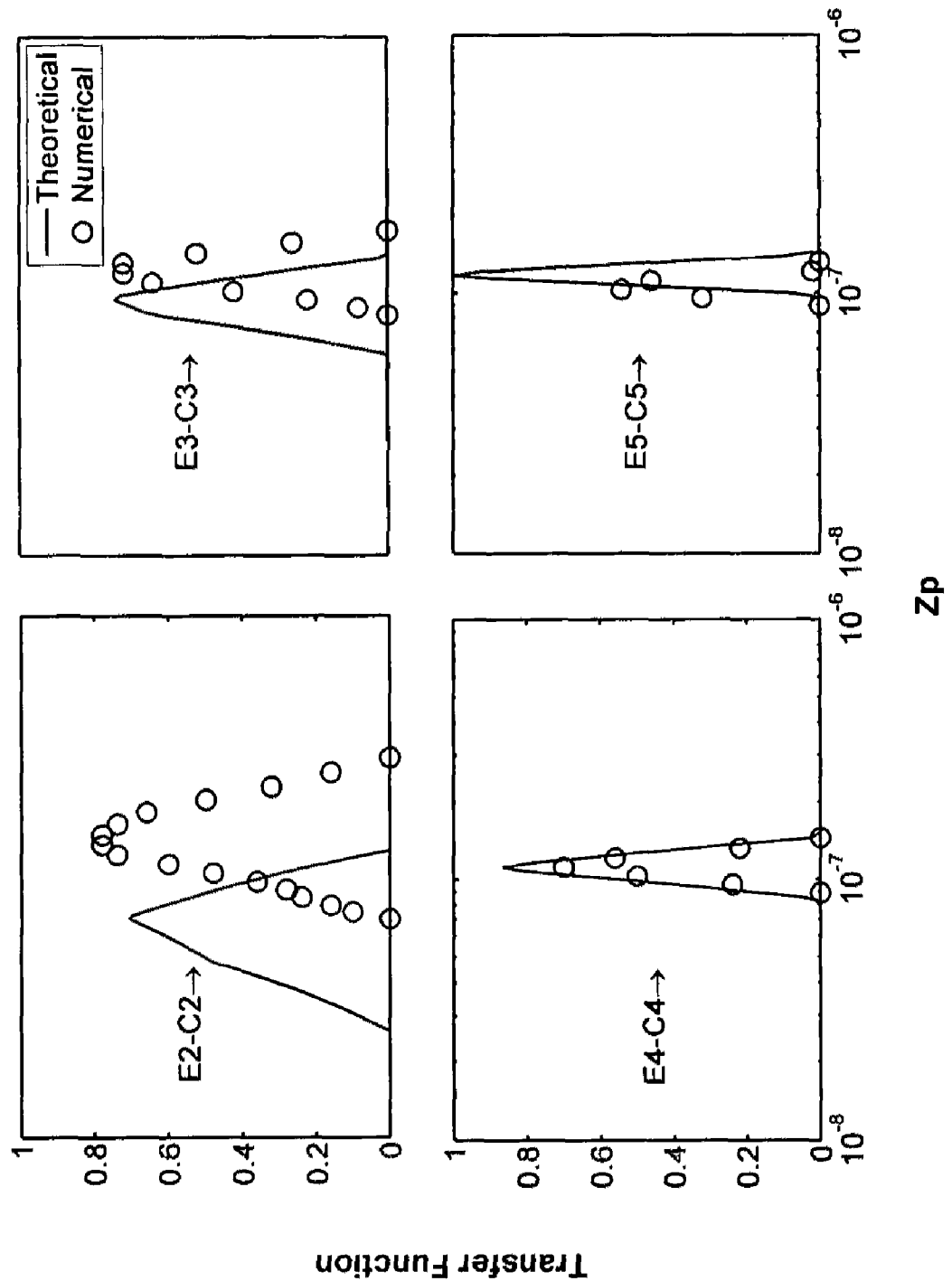
FIG. 3 illustrates a comparison of theoretical and numerical transfer functions assuming a uniform electric field and a parabolic velocity profile in the Miniature Electrical Aerosol Spectrometer classifier section.

The theoretical transfer functions for four different particle injection-collection arrangements are analyzed for comparison with the numerically obtained transfer functions. The arrangements are: E2-C2, i.e., particles injected from the $2^{nd}$ electrostatic precipitator injection channel and collected on the second collection plate (see FIG. 1); E3-C3; E4-C4; and E5-C5. As the injection channel is moved away from the collection plates, the transfer function becomes narrower, i.e. the resolution of the transfer function increases for injection channels farther from the collection plates. This is because, as the distance between the injection channels and the collection plates is increased, the sheath flow rate ($q_s$) increases, and this increases the measurement resolution (Eq. 7). Considering a parabolic velocity profile and a uniform electric field, the theoretically obtained transfer functions are seen to differ significantly from the numerically calculated transfer functions for most arrangements (FIG. 3). This suggests that a more detailed analysis of the flow and electric fields in the Miniature Electrical Aerosol Spectrometer classifier section is required.

A comparison of theoretical and numerical transfer functions show the effect of electric and flow field non-uniformity for different injection channels. A comparison of centroid mobility ($Z_p^*$), transfer function resolution ($\Re$), and transfer function height (T) is shown for the different arrangements in FIG. 4. In these calculations, the centroid mobility, $Z_p^*$, is obtained as an average of the smallest and largest particle mobilities sampled, i.e., the two mobilities forming the edges of the transfer function. The transfer function height is obtained at $Z_o^*$; and $\Re$ is the ratio of centroid mobility to the full width at the half the transfer function height.

The difference in the numerical and theoretical centroid mobilities and resolutions are seen to be higher for lower collection plate numbers (i.e., C2 and C3). This suggests that the non-uniformities in the flow and electric fields are most important close to the electrostatic precipitator section exit. A comparison of transfer function heights shows that the discrepancy is particularly enhanced for electrostatic precipitator injection channels closer to the high voltage classifier plate (i.e., E4 and E5). This is because the proximity of the classifier high voltage plate enhances electric field non-uniformity, and hence particle loss, in and near these channels. In the numerically obtained transfer functions, these losses are accounted for, but not in the theoretical model with parabolic flow and uniform electric field.

Accurate transfer function evaluation of the Miniature Electrical Aerosol Spectrometer instrument requires an improved theoretical model considering realistic approximation of the electric and flow field inside the instrument.

Non-Uniform Flow and Electric Field Model:

For accurate transfer function calculation, the flow characteristics just downstream of the electrostatic precipitator section must be considered. In addition, the net non-uniform electric field due to the different potentials on the electrostatic precipitator plates and the applied HV in the classifier section must be determined for accurate particle trajectory calculations. A simple theoretical approach is outlined to account for these force field non-uniformities.

Assuming that there are no space charge effects in the Miniature Electrical Aerosol Spectrometer classifier section, the non-uniform electric potential distribution (V) in the Miniature Electrical Aerosol Spectrometer satisfies the equation:

$$\nabla^2 V = 0. \tag{8}$$

Figure 5:
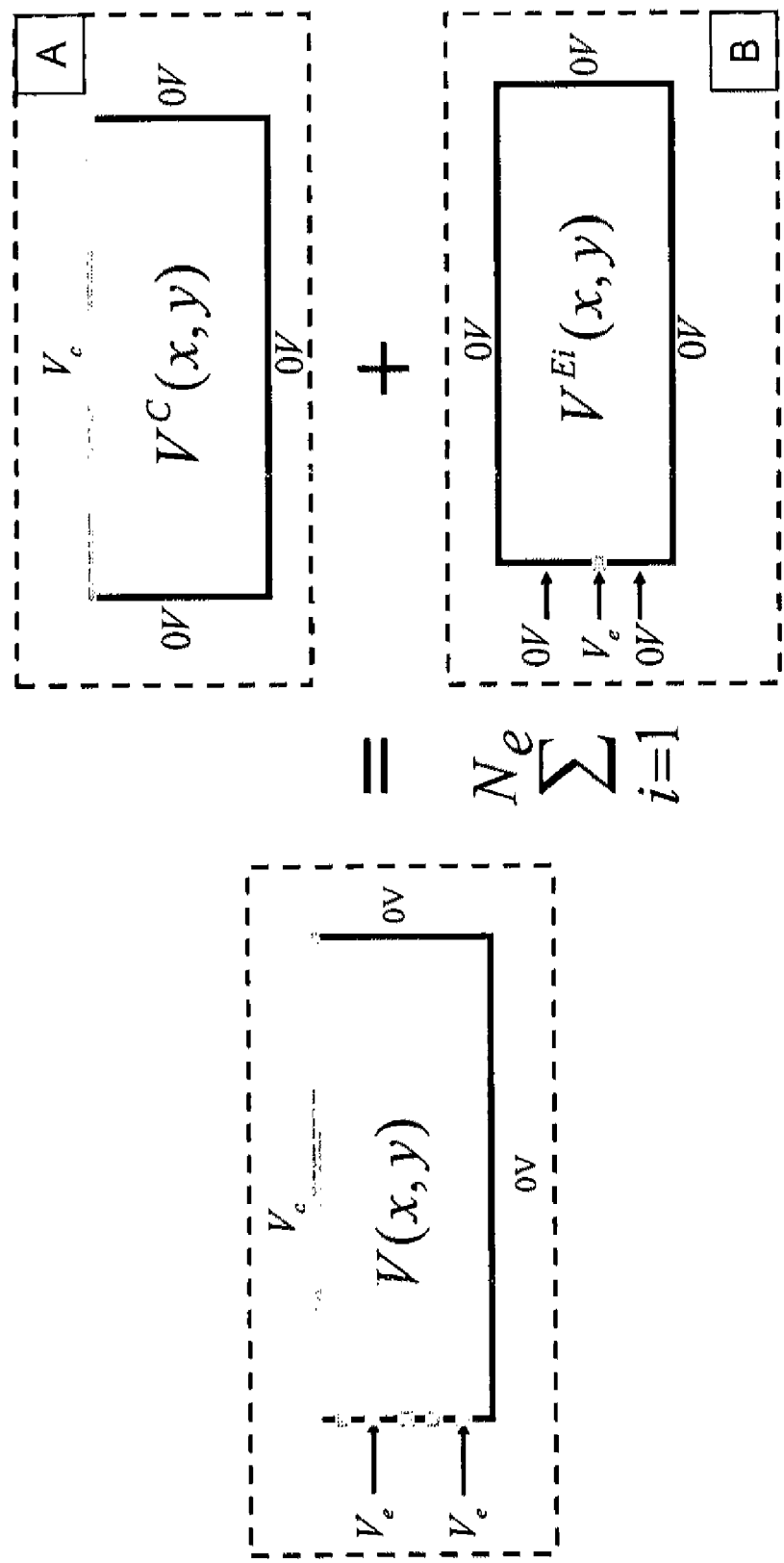
FIG. 5 illustrates a Miniature Electrical Aerosol Spectrometer classification section geometry split for theoretical non-uniform electric field calculation using a superimposition of voltages.

The electric potential has the form of the Laplace equation which is linear in nature. Thus, the electric potential field in the Miniature Electrical Aerosol Spectrometer classifier section can be obtained using the superposition of the individual contributions of the electrostatic precipitator and classifier sections. For this approach, the net classifier section potential field is obtained considering the independent presence of the classifier plate voltage and the individual electrostatic precipitator plates as illustrated in FIG. 5.

The electric field due to the classifier plate voltage ($V^C$) (case-A in FIG. 5) can be obtained from the solution to Eq. (8) with the upper edge at voltage $V_c$ and the other edges at zero potential:

$$V^C(x, y) = \sum_{n=1}^{\infty} A_n \sin\left(\frac{n\pi x}{L}\right) \sinh\left(\frac{n\pi y}{L}\right) \tag{9}$$

$$\text{where } A_n = \frac{2V_c}{n\pi} \frac{1}{\sinh\left(\frac{n\pi H}{L}\right)} [1 - (-1)^n]$$

Similarly, the electric potential contribution of the individual electrostatic precipitator plates ($V^{Ei}$) (case B in FIG. 5) is obtained considering a small section of the left side boundary, representing the electrostatic precipitator plate edge at the classifier section entrance, to be at a selected potential, $V_e$. The rest of the boundary is considered to be at zero potential. The electrostatic precipitator plate position is represented by the height of the lower and upper ends of the channel, $h_u^{i-1}$ and $h_l^i$, respectively, above the collection plate (See FIG. 2). The voltage distribution for this geometry is:

$$V^{Ei}(x, y) = \sum_{n=1}^{\infty} B_n \sin\left(\frac{n\pi y}{H}\right)\left(\exp\left(\frac{n\pi}{H}x\right) - \exp\left(\frac{n\pi}{H}(2L - x)\right)\right) \tag{10}$$

$$\text{where } B_n = \frac{2V_e}{n\pi} \frac{1}{\left(1 - \exp\left(2L\frac{n\pi}{H}\right)\right)}\left[\cos\left(\frac{n\pi h_u^{i-1}}{H}\right) - \cos\left(\frac{n\pi h_l^i}{H}\right)\right]$$

The net electric potential distribution in the classifier section, considering Ne number of electrostatic precipitator plate voltages and the classifier plate voltage, is:

$$V(x, y) = V^C(x, y) + \sum_{i=1}^{Ne} V^{Ei}(x, y) \tag{11}$$

Figure 6:
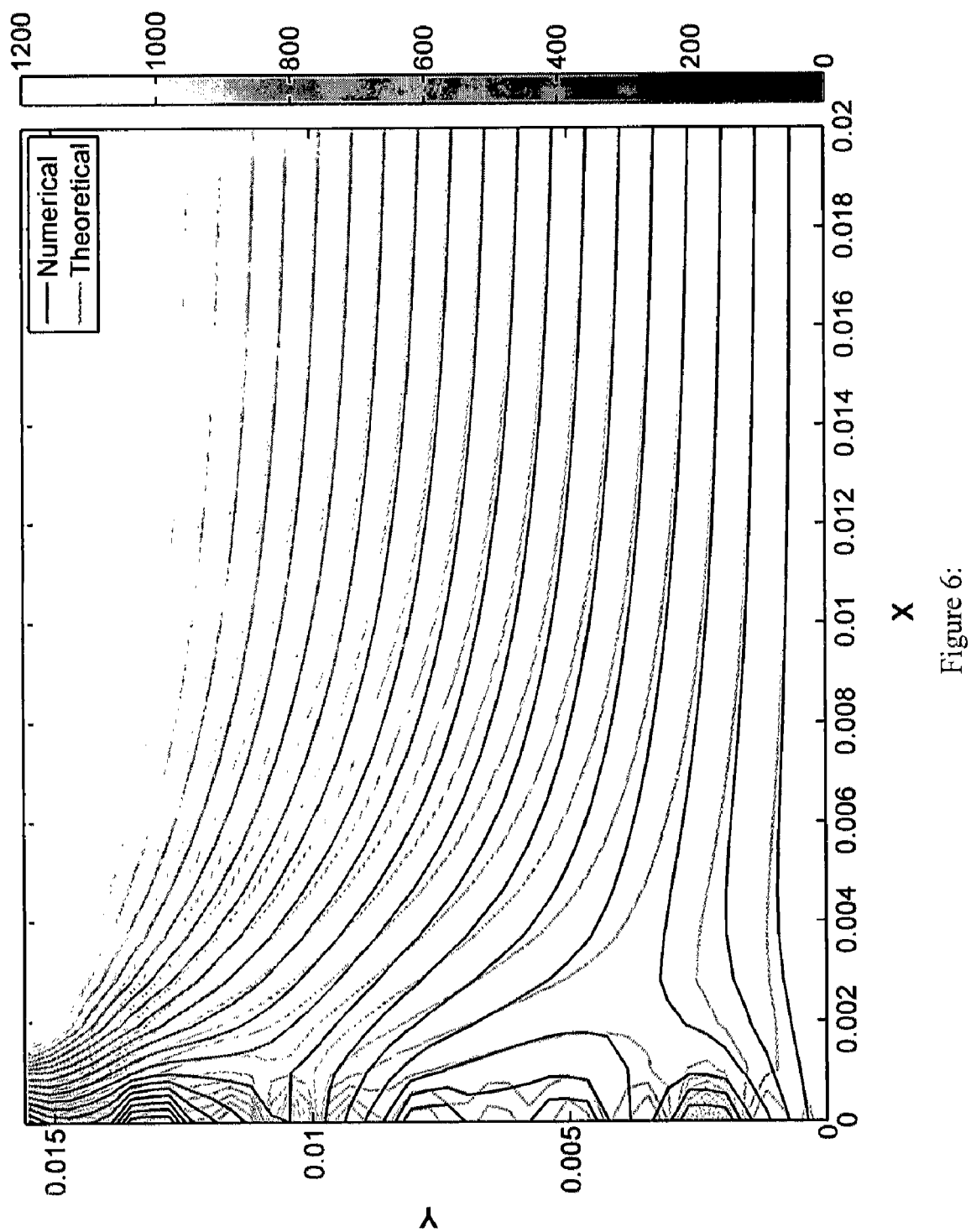
FIG. 6 illustrates a comparison of the theoretical and numerical voltage contours.

A comparison of the electric potential fields obtained from theoretical modeling and numerical simulations is complicated by their different boundary conditions of zero potential and zero flux, respectively at the classifier exit. To overcome this discrepancy between the two approaches, the length of the classifier section in the theoretical model is assumed to be nearly double (~2 L) that in the numerical simulations. For this geometry, over a classifier section of length L, the theoretical potential field will be consistent with an exit boundary condition of zero electric potential flux. A comparison of the electric potential fields obtained from theoretical and numerical models is shown in FIG. 6. For these calculations, the classifier HV is set to 1200V and the second and fifth electrostatic precipitator plates (E2 & E5; FIG. 1) are set to 350V. The theoretical potential fields compare well with the numerical results. The theoretical model is seen to reasonably capture the non-uniformities in the electric potential fields at the electrostatic precipitator exit, particularly in the vicinity of the classifier HV plate.

In addition to electric field non-uniformity, accurate particle trajectory calculations require a realistic representation of flows in the vicinity of the electrostatic precipitator section exit. Assuming laminar, incompressible flow, a simplified model for the flow field in the classifier section is obtained considering parabolic velocity profiles for flow from the different electrostatic precipitator channels and converting the individual profiles to one parabolic velocity profile over the entire classifier channel after some mixing length. This simplified flow field assumption will accurately capture the velocity profile at the entrance of the classifier section where the non-uniformity in the electric fields is most intense.

The individual parabolic velocity profiles from the different electrostatic precipitator channels can be combined to obtain the net velocity profile in the classifier section [$u^E(x, y)$] as:

$$u^E(x, y) = \sum_{i=1}^{Ne+1} \frac{6u_{avg}^E}{(h_u^i - h_l^i)^2} (y - h_l^i)$$ (12)

$$(h_u^i - y)[U(y - h_l^i) - U(y - h_u^i)][U(-x + p(h_l^i - h_u^{i-1}))]$$

where $u_{avg}^E$, is the average flow velocity through the electrostatic precipitator injection channels and $N_e$ is the number of electrostatic precipitator plates and U is a Heaviside step function. The last step function, $U(-x+p(h_l^i-h_u^{i-1}))$, ensures that the above velocity profile is limited to a region of $x<p(h_l^i-h_u^{i-1})$, where $(h_l^i-h_u^{i-1})$ is the thickness of the electrostatic precipitator plate and p is a mixing length scale that determines the distance along the flow direction over which this electrostatic precipitator-based flow field is valid; i.e., the region over which the individual electrostatic precipitator flows are prominent. Based on subsequent calculations with values of p ranging from 1 to 3 and it was seen that calculated transfer function characteristics ($Z_p^*$, $\Re$, and T) were largely independent of the exact value of p. The variation of the value of p with flow rate was seen to be very small in the laminar flow region, and in the range of p=1-3, the transfer function characteristics were not significantly affected by the exact value of p. Therefore, for all subsequent transfer function calculations a constant value of p=2 was assumed.

Beyond the electrostatic precipitator-based flow region, the velocity distribution is assumed to be parabolic over the entire classifier section height and is represented as:

$$u^C(x, y) = \frac{6U_{avg}^C}{H^2} y(H - y)U(x - p(h_l^i - h_u^{i-1}))$$ (13)

where $u^C(x,y)$ is the velocity in the classifier section away from the electrostatic precipitator-based flow region, and $U_{avg}^C$ is the average velocity through the classifier section, which is same as the average velocity through the Miniature Electrical Aerosol Spectrometer. Eqs. (12) and (13) can be summed to obtain the velocity field [$u^{net}(x,y)$] in the Miniature Electrical Aerosol Spectrometer classifier section.

Figure 7:
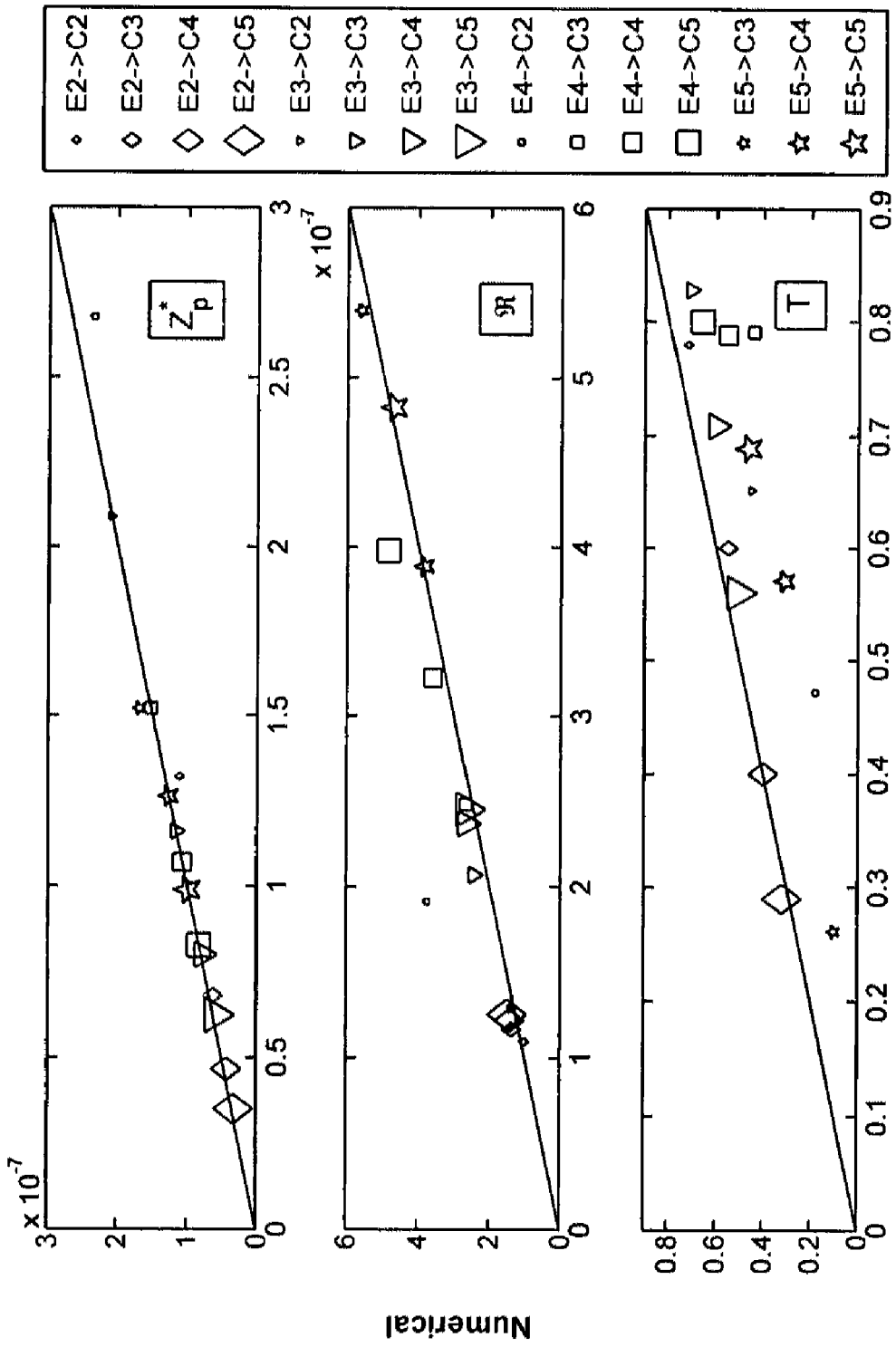
FIG. 7 illustrates a comparison of theoretical and numerical values of $Z_p^*$, $\mathfrak{R}$, and T for the non-uniform electric potential and flow field model.

The stream and electric flux functions in the classifier section can be obtained from the net velocity field (Eqs. 12 and 13) and electric potential field (Eq. 11), respectively. Particle trajectories in the classifier section can then be calculated using Eq. 1. To determine the fate of particles in the classifier section, N contours of $\psi+Z_p\phi$ are calculated at equal stream function intervals in the electrostatic precipitator injection channel. Each contour line represents a sample particle trajectory of a selected mobility within a fraction of flow ($q_a/N$) in the electrostatic precipitator section. The fraction of contour lines that directly reach the collection plate determines the transfer function height for that selected mobility. This calculation is repeated for varying particle electrical mobilities to obtain the entire theoretical transfer function for a selected injection channel and collection plate. The centroid mobility, resolution, and height of the theoretically calculated transfer function for the non-uniform flow and electric fields are compared with those obtained numerically (FIG. 7). Comparisons are made for a design with electrostatic precipitator channels spaced 2 mm apart, electrostatic precipitator plate thickness of 0.7 mm, collection plate lengths of 1 cm, and a flowrate of 1 LPM.

Figure 4:
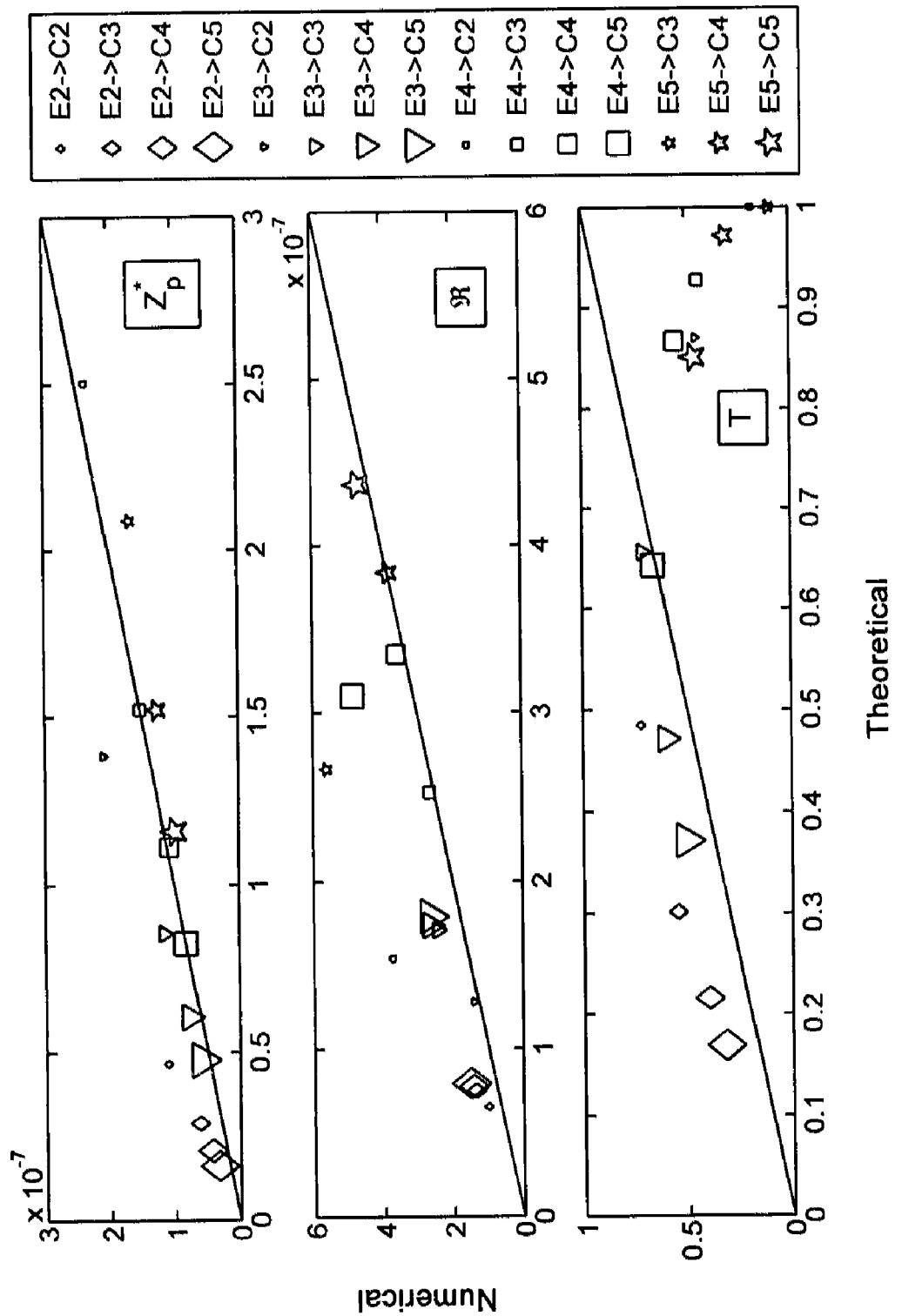
FIG. 4 illustrates a comparison of numerical and theoretical values of $Z_p^*$, $\mathfrak{R}$, and T for a uniform electric field and a parabolic velocity profile.

The theoretical $Z_p^*$, and $\Re$ based on the non-uniform model are seen to better match the numerical results in comparison to the simple case of parabolic flow and uniform electric field (FIG. 4). The transfer function heights are, however, over-predicted by the theoretical calculations, particularly for injection channels closer to the classifier HV plate. This suggests that, in addition to the classifier section non-uniformities, there is also a need to account for the effect of the classifier HV on the electric field, and hence particle trajectories, inside the electrostatic precipitator injection channel.

Figure 8:
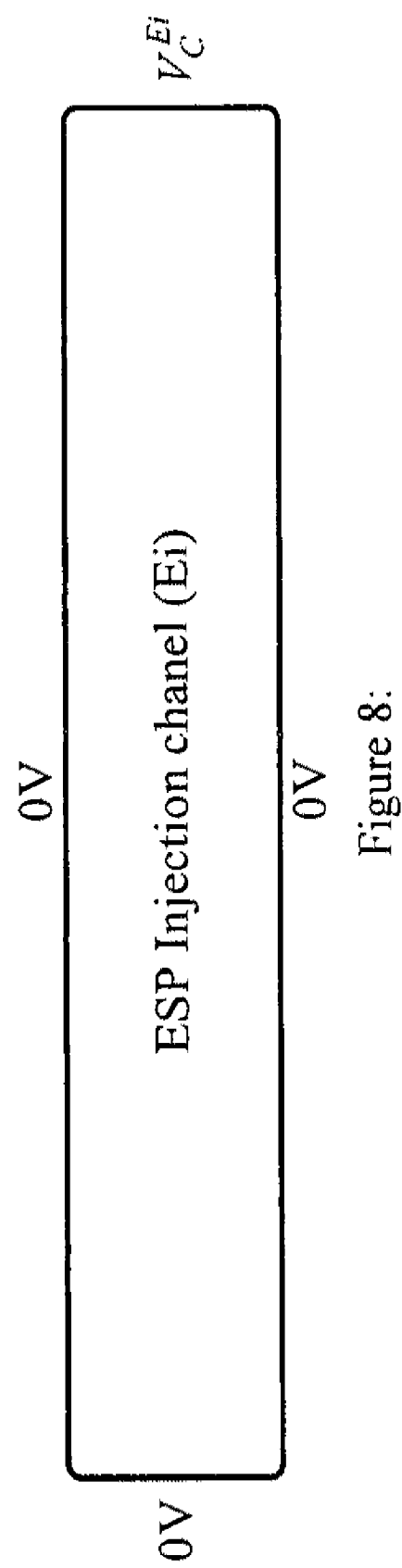
FIG. 8 illustrates an Electrostatic Precipitator injection channel modeled as a rectangular channel.

To calculate particle loss in the electrostatic precipitator section, the electric potentials inside the injection channel were obtained for a rectangular channel with zero potential on all boundaries except the electrostatic precipitator outlet edge (FIG. 8). The boundary condition at the electrostatic precipitator outlet is largely determined by the classifier voltage, and is difficult to obtain theoretically. Here, the electric potential distribution in the combined regions of electrostatic precipitator and classifier sections was numerically calculated by solving Eq. (8). The resultant electric potential distribution ($V_c^{Ei}$) at the exit of the injection channels was used as the boundary condition to obtain the electric potential distribution in the electrostatic precipitator channel. Particle trajectories through the electrostatic precipitator channel were then obtained using the same procedure described for the calculation of the theoretical transfer function. Particle penetration through an electrostatic precipitator injection channel was determined from the fraction of flow from where particles successfully exited the channel.

Figure 9:
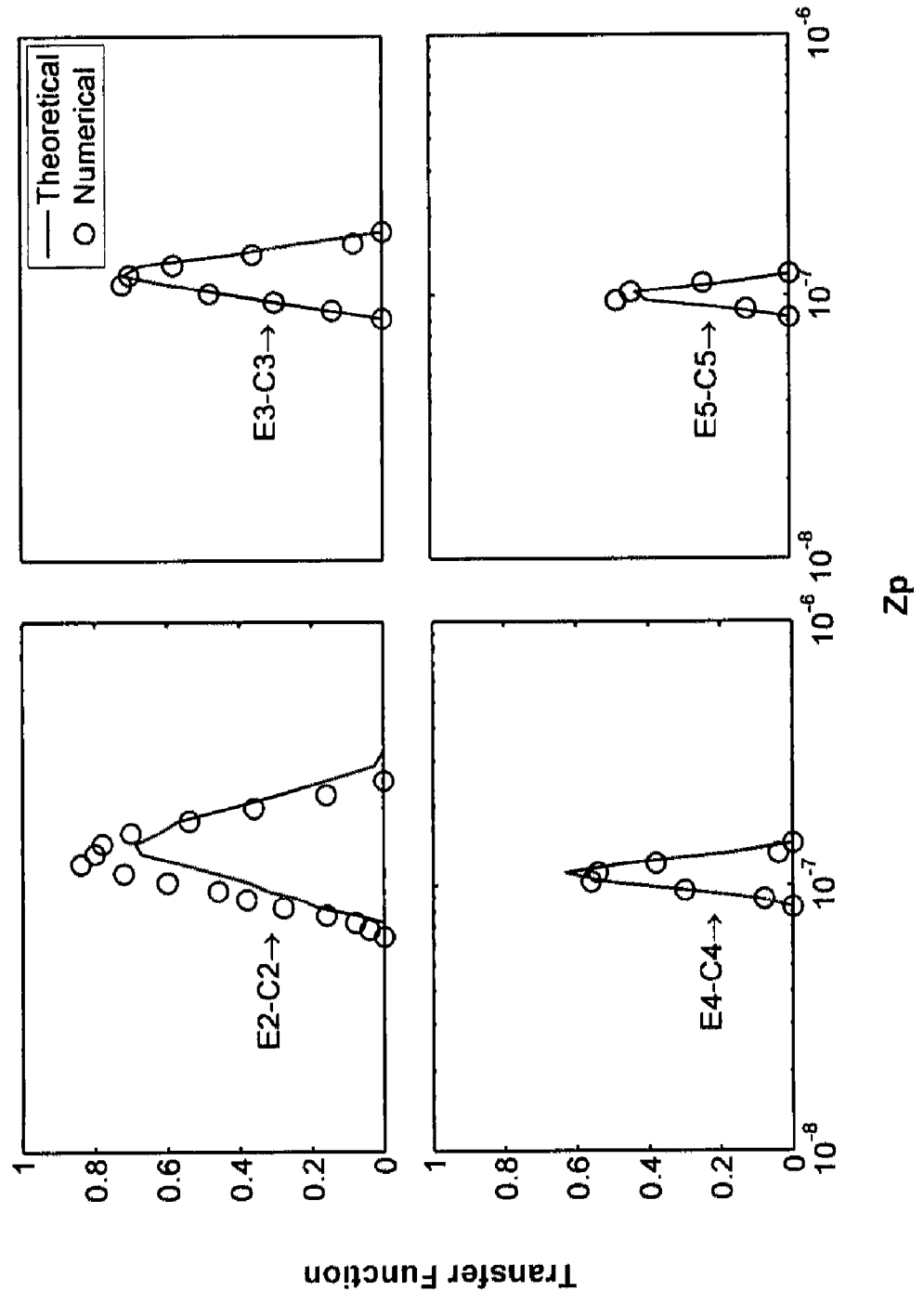
FIG. 9 illustrates a comparison of theoretical and numerical transfer functions.
Figure 10:
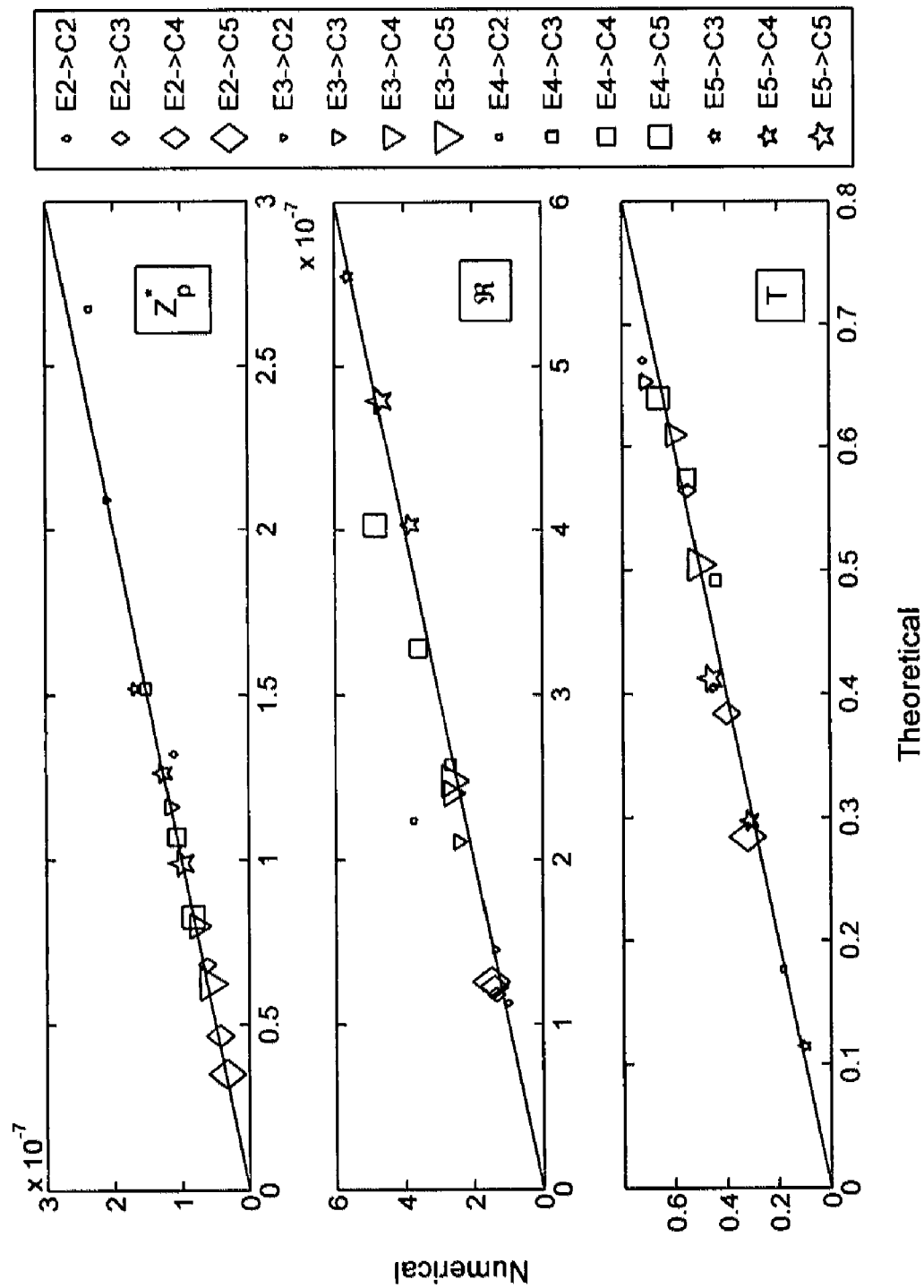
FIG. 10 illustrates a comparison of numerical values of $Z_p^*$, $\mathfrak{R}$ and T with the theoretical values accounted for with particle penetration.
Figure 11:
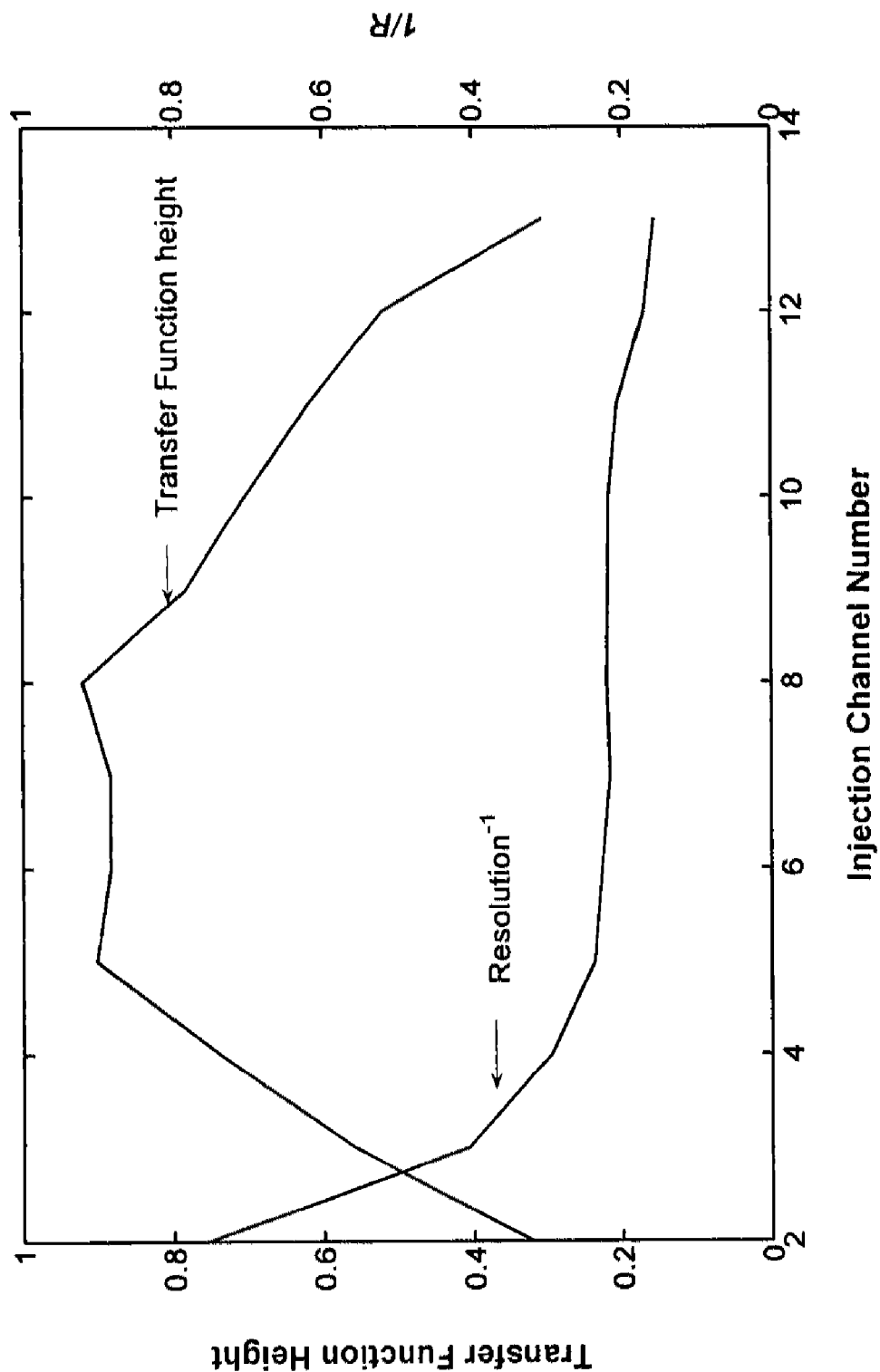
FIG. 11 illustrates that the resolution and transfer function height are dependent on the injection channel number.

Accounting for the calculated particle loss in the electrostatic precipitator channels, the transfer functions for E2-C2, E3-C3, E4-C4 and E5-C5 are shown in FIG. 9. It is seen that the theoretical and numerical transfer functions match very well. A comparison of the theoretical model performance for prediction of $Z_p^*$, $\Re$, and T for a wide range of electrostatic precipitator and classifier section combinations is shown in FIG. 10. It is seen that for all cases studied the theoretical transfer function characteristics, including transfer function height, matched well with numerical predictions. This analysis also shows that the transfer function height increases for electrostatic precipitator channels away from both the collection plate and the classifier HV plate. This is because, for injection channels close to the collection plate, the transfer function is broad due to the reduced sheath flow and only a small fraction of the particles at the peak mobility are captured on the collection plate. For channels close to the classifier HV plate, the non-uniformity in the electric fields negatively influences particle penetration through the electrostatic precipitator channels. The resolution of measurement, however, continuously increases away from the collection plate, as expected from Eq. (7). It is possible to locate the injection channel close to the classifier plate by maintaining both plates of the injection channel at high voltage, consistent with the classifier plate voltage. This, however, is seen to result in significant particle loss in the region between the electrostatic precipitator plates and the upstream plates (upstream of the electrostatic precipitator) due to the strong electric fields in that region, and is thus, not considered for further analysis.

Figure 12:
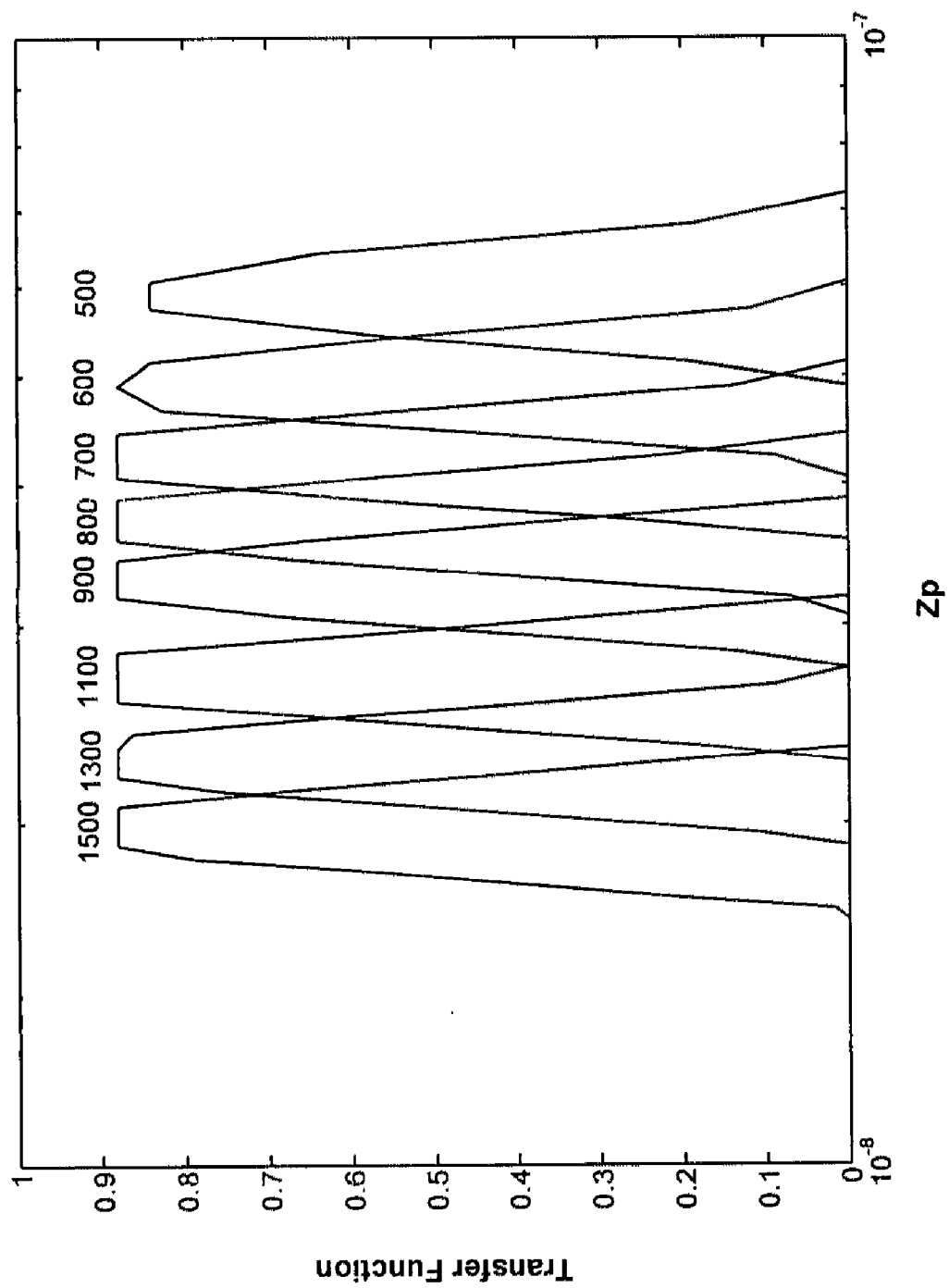
FIG. 12 illustrates the theoretical transfer functions for a E8-C5 configuration for varying classifier voltages and a flow rate of 0.5 LPM with 350V on the Electrostatic Precipitators.
Figure 13:
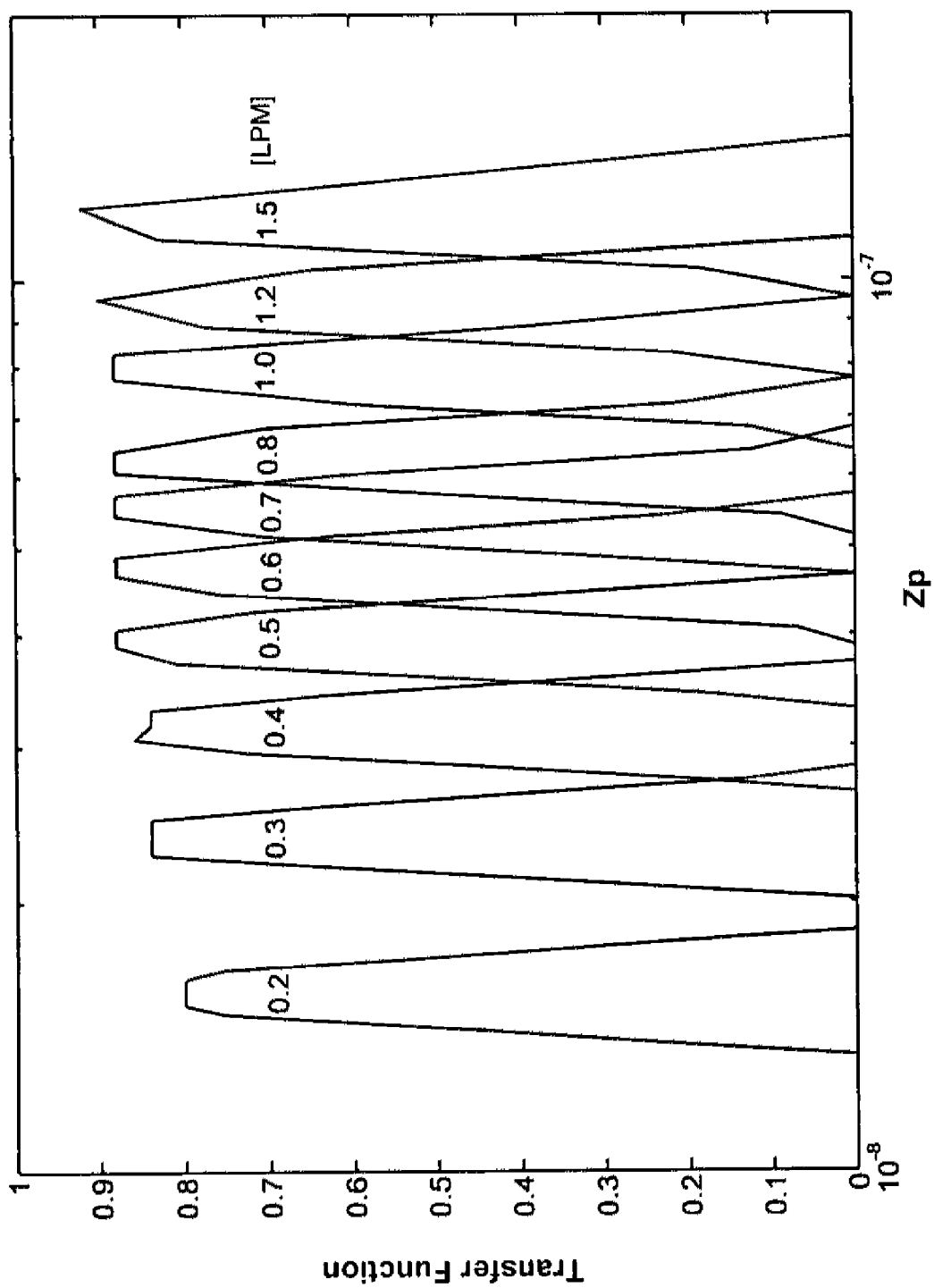
FIG. 13 illustrates the theoretical transfer functions for the E8-C5 configuration for varying flow rates through the instrument with classifier and Electrostatic Precipitators at 750V and 300V respectively.
Figure 14:
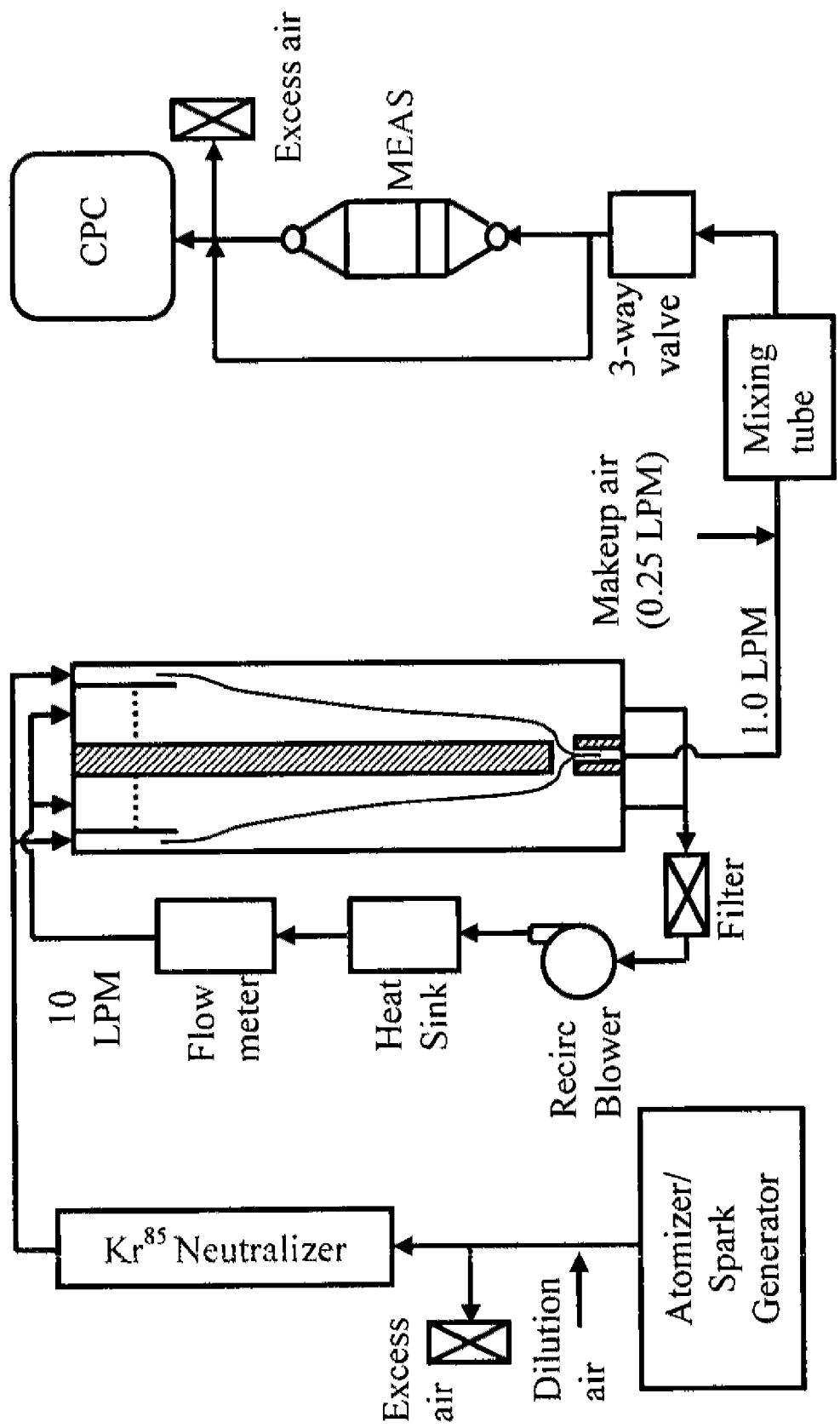
FIG. 14 illustrates a schematic diagram of a set-up used for testing the individual components of a Miniature Electrical Aerosol Spectrometer.
Figure 15:
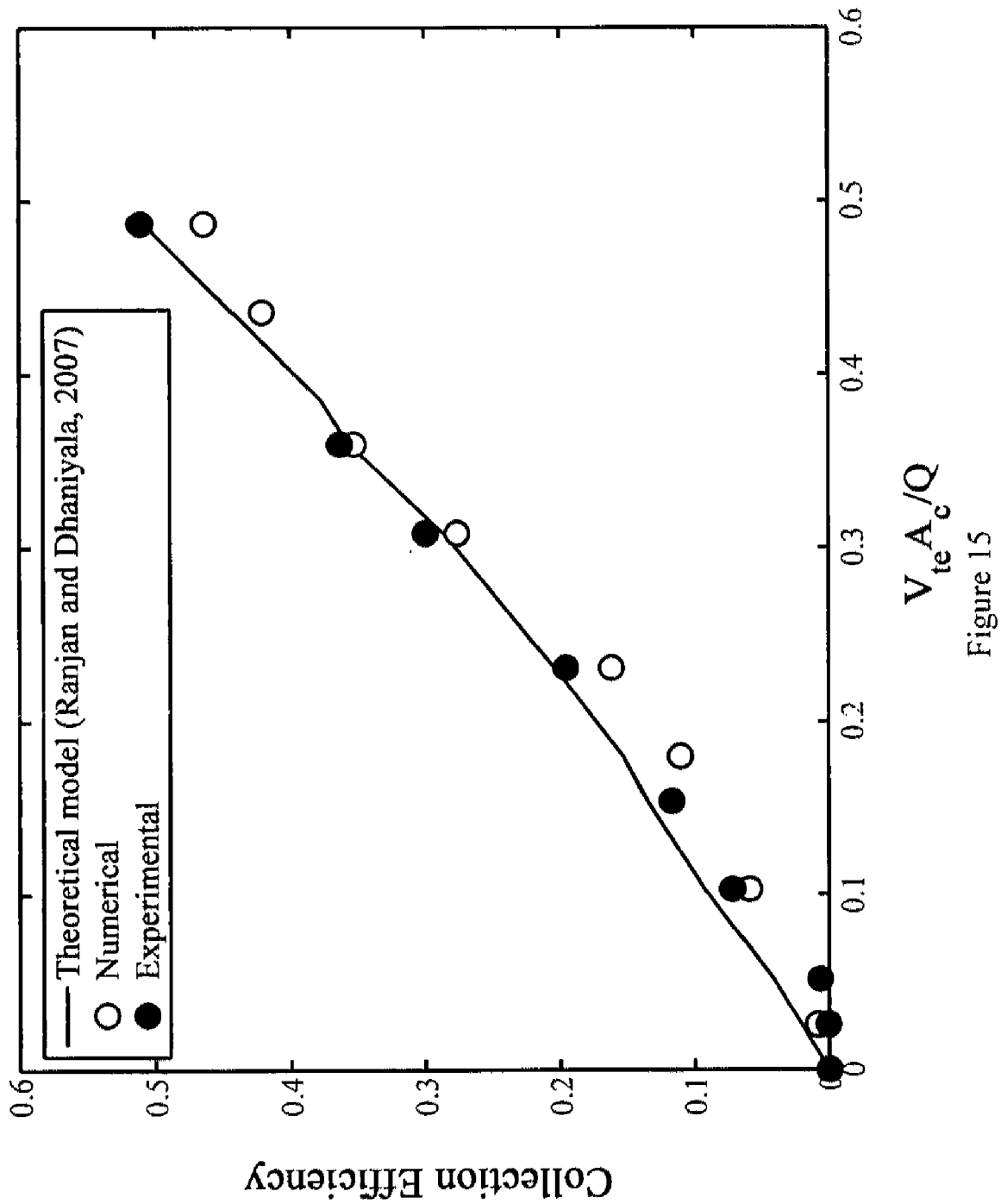
FIG. 15 illustrates a comparison between the numerical and experimental collection efficiencies of the classifier section with grounded electrostatic precipitator section and 85 nm test particles.

To determine if an optimal choice of injection channel exists, a Miniature Electrical Aerosol Spectrometer design with 15 injection channels spaced 1 mm apart with electrostatic precipitator plate thickness of 0.1 mm and a flow rate of 0.5 LPM is considered. The classifier and electrostatic precipitator voltages were chosen to be 750V and 300V, respectively, and the collection plates were chosen to be 1 cm long with 1 mm gap between them. The resolution and transfer function heights from the theoretical model are shown in FIG. 12. As expected, the best resolution is obtained for injection channels farthest from the collection plates. For these injection channels, however, particle penetration values are lowered due to the influence of the classifier plate voltage. The optimal injection channels are seen to be in the range of E4 to E8. For these channels, particle penetration is largely unaffected by the electric field non-uniformity, while the available sheath to aerosol flow ratio ensures reasonable resolution. The theoretical transfer functions for injection through channel E8 and collection on plate C5 for varying classifier plate voltages and instrument flowrates is shown in FIGS. 13 and 14. The transfer functions indicate that under optimal operation, Miniature Electrical Aerosol Spectrometer can have high particle transmission efficiency and resolution. Careful selection of Miniature Electrical Aerosol Spectrometer flow rates or classifier voltages can result in equally spaced, minimally-overlapping transfer functions that should enable relatively easy data inversion.

For practical applications, the instrument width and flow velocity should be selected such that the desired lower measurement limit of particle concentration is consistent with the electrometer sensitivity and noise characteristics. Typical lab-built electrometers have a lower detection limit of ~1 fA. The maximum flow rate through the instrument is limited by the requirement of laminar flow in the instrument. The presence of the electrostatic precipitator plates may result in non-laminar flow at Reynolds numbers lower than that for smooth channels, and the exact limits of flow rate operation must be determined experimentally. Assuming a flow transition Reynolds number of ~1000, the maximum flow rate through the instrument for the design shown in FIG. 1 (classifier channel height 1.55 cm, six electrostatic precipitator channels of 2 mm spacing, and electrostatic precipitator plate thickness of 0.7 mm) is ~30 LPM. For these conditions, the minimum concentration required for particle detection on $3^{rd}$ collection plate with 500V on classifier section and 350V on electrostatic precipitator channel (corresponding to a mean particle size collected of ~40 nm) is ~1E4 $cm^{-3}$. Increasing the collection plate size or the overall instrument width will lower the concentration detection limit.

Design Description

An exemplary Miniature Electrical-mobility Aerosol Spectrometer was fabricated for experimental validation of theoretical predictions. The inlet section in the Miniature Electrical-mobility Aerosol Spectrometer is required to transition the flow from a circular cross-section to the rectangular cross-section at the entrance of the electrostatic precipitator section. To minimize recirculation regions, the inlet section is designed to gradually change from a circular to a rectangle cross-section. An optimal expansion angle of ~7 degrees will minimize recirculation within the inlet, but this will result in an impractically long section. Instead, an expansion angle of 18 degrees is chosen and a wire mesh is located in the middle of the 10 cm long section to provide pressure drop and promote flow uniformity across inlet section exit.

In an exemplary Miniature Electrical-mobility Aerosol Spectrometer, the electrostatic precipitator section is designed with five parallel electropolished stainless steel plates that are 2 cm long, 5 cm wide, and 0.7 mm thick, and spaced 2 mm apart. For electrical connectivity, the plates are individually connected to electrical wires through a screw and spring setup on the sides of the instrument. An ultraminiature voltage amplifier (EMCO Inc.) is used to set the voltage on the electrostatic precipitator plates. The electrostatic precipitator plate voltages are chosen such that charged particles are electrostatically filtered through all the electrostatic precipitator channels except one selected injection channel. For typical operation, the potential difference in the electrostatic precipitator channels must result in the capture of sub-500 nm singly-charged particles, while remaining below the breakdown potential. A high voltage source is used through a voltage distributor to set voltages on the electrostatic precipitator plates. For handling safety, the electrostatic precipitator section and classifier section are housed in an external insulated unit made of Delrin®.

The classifier section of the Miniature Electrical-mobility Aerosol Spectrometer consists of a set of five collection plates, spaced 1 mm apart, located across a classifier plate that is maintained at high voltage. Electropolished stainless steel rectangular plates of 1 cm length, 5 cm width, and 0.7 mm thickness are used as collection plates.

The Miniature Electrical-mobility Aerosol Spectrometer particle capture characteristics are complicated by the non-uniform nature of the electric and flow fields in the classifier section. The details of the calculation of electric and flow fields in the Miniature Electrical-mobility Aerosol Spectrometer are provided in Ranjan and Dhaniyala (2007), hereby incorporated herein by reference and only a brief overview is given here. In the absence of space charge effects, the non-uniform electric potential field in the Miniature Electrical-mobility Aerosol Spectrometer classifier section is obtained by solving the Laplace equation with appropriate boundary conditions. For accurate flow field calculations in the classifier section, the non-uniformities in the vicinity of the electrostatic precipitator section exit are considered. The velocity profile in the individual electrostatic precipitator channels is assumed to be parabolic and these profiles are combined using a Heaviside step function to represent the velocity profile in the vicinity of the electrostatic precipitator exit; while in the rest of the classifier section flow is represented as a single parabolic velocity profile over the entire channel. Electric flux function and stream functions were then calculated analytically in the classifier geometry and contours of $\psi+Z_p\phi$ are then used to determine particle trajectories in the instrument. The Miniature Electrical-mobility Aerosol Spectrometer transfer function was calculated as the fraction of charged aerosol particles entering the electrostatic precipitator injection channel that are captured on the collection plate. The transfer functions in conjunction with appropriate data inversion routines are used to determine the size distribution from the electrometer signals.

In addition to the theoretical modeling, the Miniature Electrical-mobility Aerosol Spectrometer performance is also obtained from computational fluid dynamics (CFD) simulations using the software FLUENT (FLUENT Inc., NH). A User Defined Function (UDF) code is used to accurately account for slip correction and the effect of electric field on particle trajectories in the instrument (See Ranjan and Dhaniyala, 2007, hereby incorporated herein by reference). The numerical transfer functions compares well with theoretical predictions.

MEAS Performance Validation

Validation of theoretical and numerical Miniature Electrical-mobility Aerosol Spectrometer sizing performance requires a number of different experiments. In the first test, the overall collection efficiency of the classifier section is measured. For this test, all electrostatic precipitator plates are grounded, thus permitting the injection of charged particles from all electrostatic precipitator channels into the classifier section. The total collection efficiency can be determined from measurement of particle concentrations upstream and downstream of the instrument and compared with the theoretically predicted collection efficiency. In the second test, the voltage on the electrostatic precipitator plates are set such that particles are injected only through one channel and the experimentally obtained classifier section collection efficiency is compared with the theoretically predicted values. In the third test, an electrometer is connected to a collection plate and the flow rate through Miniature Electrical-mobility Aerosol Spectrometer is varied to capture particles over different mobility ranges on that collection plate. The resultant measured size distribution is compared with measurements of the scanning mobility particle spectrometer (SMPS).

Performance Evaluation of the MEAS Classifier Section

Figure 17:
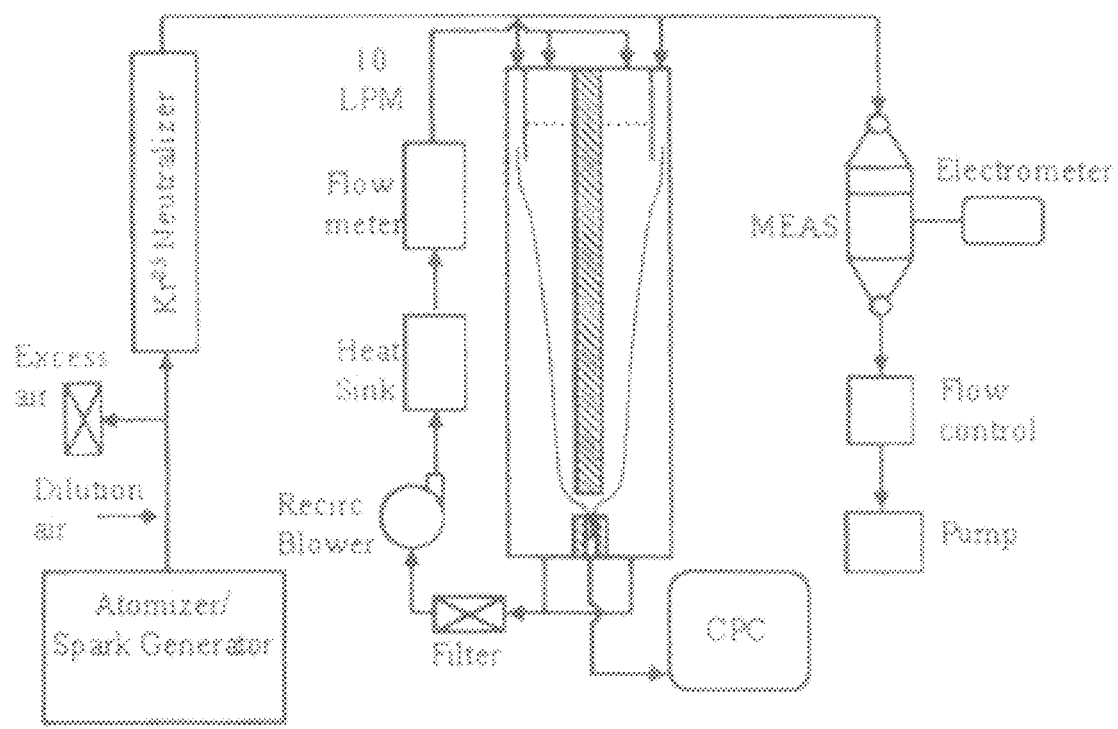
FIG. 17 illustrates a setup used for size distribution measurements with a Miniature Electrical Aerosol Spectrometer.
Figure 18:
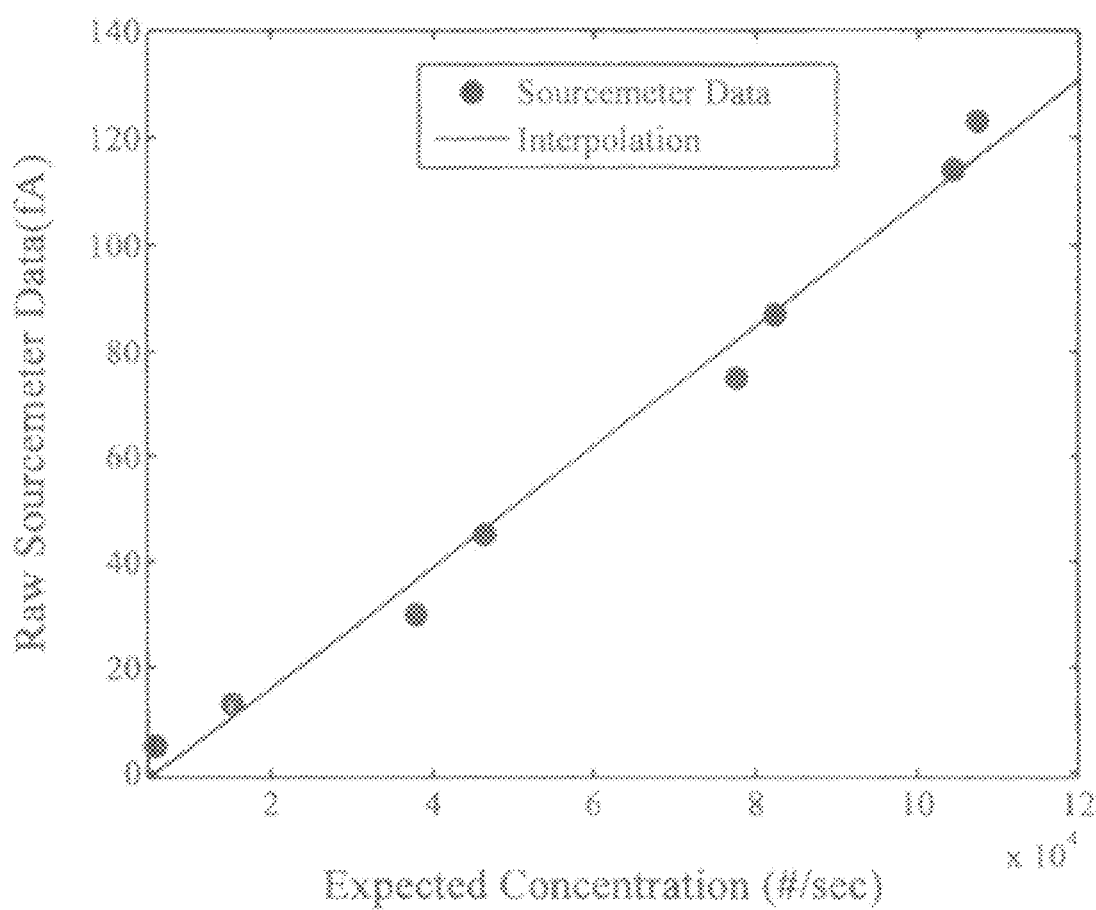
FIG. 18 illustrates a comparison of a raw electrometer signal with expected particle concentration on the collection plate.

The setup used for testing the performance of the classifier section is shown in FIG. 17. The combination of a particle source (spark discharge generator; Palas GFG 1000, Karlsruhe, Germany) and a differential mobility analyzer (operated at 1:10 flow ratio) is used to generate carbon particles over a narrow range of electrical mobilities with a mean size of ~85 nm. Particle concentrations upstream and downstream of the Miniature Electrical-mobility Aerosol Spectrometer were measured using a condensation particle counter (TSI CPC 3010) to calculate the Miniature Electrical-mobility Aerosol Spectrometer collection efficiency as a function of the classifier plate voltage.

A comparison of the measured collection efficiency and the numerical and theoretical predictions of the classifier section collection efficiency is shown in FIG. 4. The parameter $V_{te}A_c/Q$ is used for the comparison tests; where $V_{te}$ is the electrostatic terminal velocity, $A_c$ is the collection area, and $Q$ is the flow rate through the instrument. This parameter represents the collection efficiency for a uniform electric field and plug flow condition. The experimental results are seen to compare well with the numerical and theoretical predictions except at small classifier voltages, where the theoretical model slightly overestimates collection efficiency. The slight discrepancy between the experimental results and theory could be due to the finite width of the "monodisperse" particle size distribution output from the differential mobility analyzer. This test validates the performance of the classifier section without considering the electrostatic precipitator voltages.

Performance Evaluation of the MEAS ESP Section

In the next test, the performance of the electrostatic precipitator section is analyzed by injecting particles through the third injection channel from the collection plate into the classifier region. The experimental setup shown in FIG. 3 is used again for these experiments. Particles of 100 nm diameter are selected to be output from the differential mobility analyzer and the Miniature Electrical-mobility Aerosol Spectrometer classifier section voltage is varied. The measured Miniature Electrical-mobility Aerosol Spectrometer particle penetration is then compared against the numerical and theoretical predictions.

Figure 19:
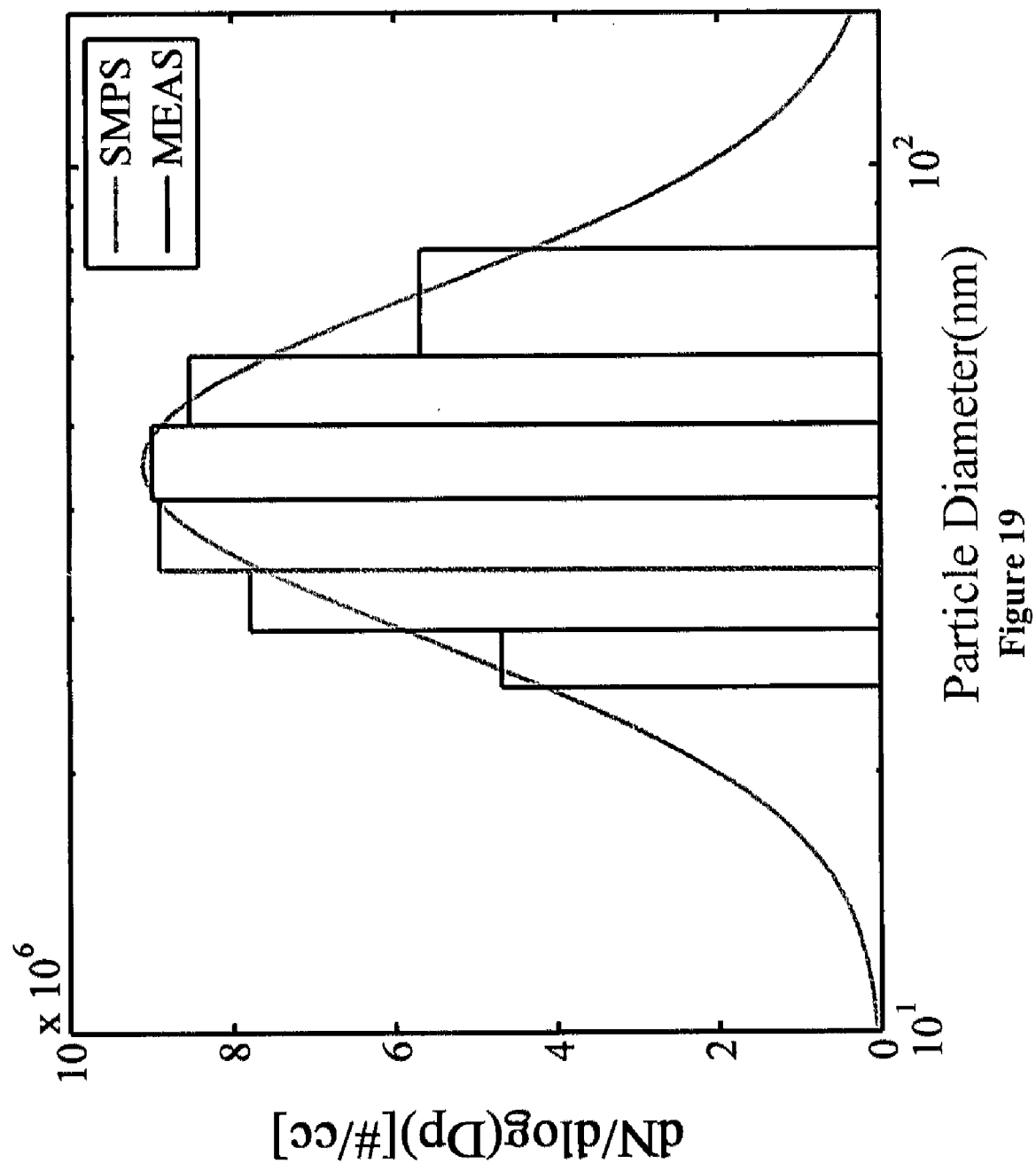
FIG. 19 illustrates the particle size distribution comparison of a Miniature Electrical Aerosol Spectrometer and Scanning Mobility Particle Spectrometer using laboratory-generated aerosol.

As seen in FIG. 19, the numerical and theoretical collection efficiencies largely match experimental data. The observed difference in the experimental and numerical results for low voltages (i.e., small values of the parameter $V_{te}A_c/Q$) is, again, possibly due to the finite resolution of the differential mobility analyzer transfer function upstream of the Miniature Electrical-mobility Aerosol Spectrometer. This result validates the theoretical modeling approach to calculate particle trajectories within the instrument and to predict the performance of electrostatic precipitator and classifier section in the Miniature Electrical-mobility Aerosol Spectrometer.

Measurement and Comparison of Particle Size Distribution by Miniature Electrical-Mobility Aerosol Spectrometer To test the performance of the integrated Miniature Electrical-mobility Aerosol Spectrometer instrument, the transfer function of the different collection stages must be experimentally determined and compared with numerical results. Such measurements are very difficult for electrometer-based instruments and, hence, here size distribution measurements made using Miniature Electrical-mobility Aerosol Spectrometer are used to validate the instrument transfer function calculation. Due to the availability of only one electrometer, the size distribution measurements were made by varying one of the instrument parameters controlling the collected mobility range. In the Miniature Electrical-mobility Aerosol Spectrometer, the collected mobility range depends on the classifier plate voltage, flow rate through the instrument, and injection channel. Changing the classifier plate voltage was observed to result in electrometer noise as the classifier channel acts as a large capacitor with a certain time constant. This also slows the electrometer response time. Size distribution measurements obtained by varying the electrostatic precipitator injection channel will be limited by the number of electrostatic precipitator channels. Changing electrostatic precipitator voltages increases electrometer noise. A change in flow rate is seen to be most suitable for size distribution measurements with Miniature Electrical-mobility Aerosol Spectrometer using only one electrometer. The flow rate through the instrument is stepped up gradually to cover the entire size range for ultrafine particles with a flow rate in the range of 0.1-5 LPM. The flow in the instrument is laminar and uniform throughout the instrument.

Figure 20:
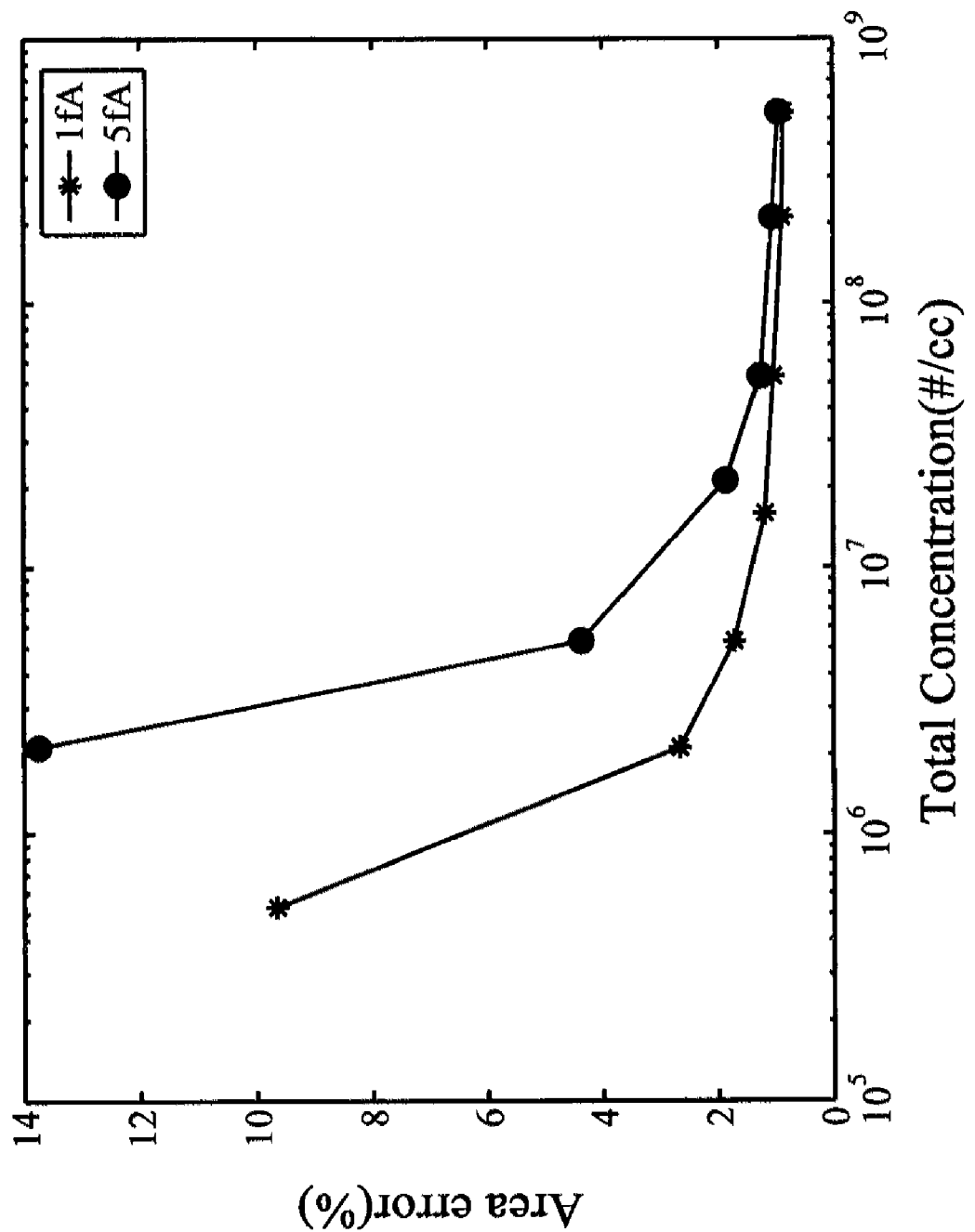
FIG. 20 illustrates the percentage area error after inversion as a function of total particle number concentration.
Figure 21:
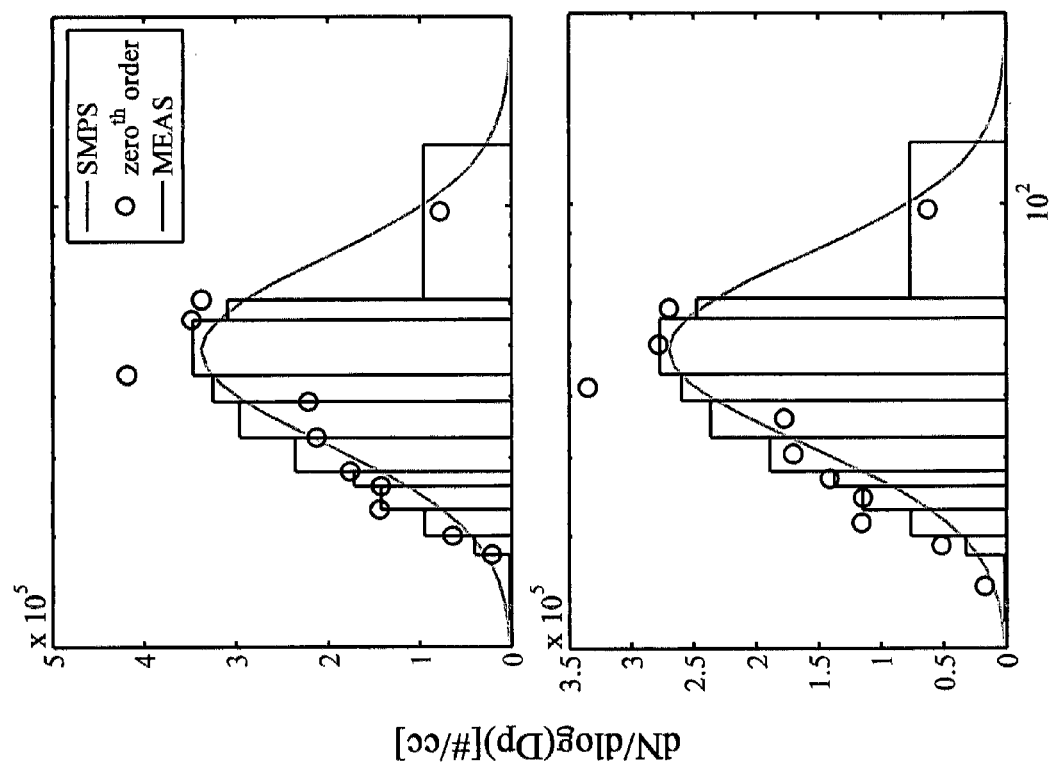
FIG. 21 illustrates a comparison of Miniature Electrical Aerosol Spectrometer and Scanning Mobility Particle Spectrometer measurements of particle size distributions from a diesel generator.

To test the consistency of the electrometer signal, the electrometer response was recorded for varying upstream particle concentrations. The experimental setup for this test was the same as that used earlier (FIG. 20). The electrometer (Keithley sourcemeter, Model 6430) was connected to the third collection plate from the electrostatic precipitator channel side. The measured signal was compared against the expected particle concentration collected on the $3^{rd}$ collection plate of the classifier section. The electrostatic precipitator plates were set to 500V with the injection channel chosen as the $3^{rd}$ channel above the collection plates. The classifier plate was set to 1000V and flow rate through the instrument was 1 LPM. The particle size distribution upstream of Miniature Electrical-mobility Aerosol Spectrometer was monitored with a Scanning Mobility Particle Spectrometer system and the Miniature Electrical-mobility Aerosol Spectrometer electrometer signal was recorded for varying upstream particle concentration. The expected number of particles captured on the $3^{rd}$ collection plate was calculated using the theoretical transfer function (See Ranjan and Dhaniyala, 2007, hereby incorporated herein by reference) and the Scanning Mobility Particle Spectrometer particle size distribution. A comparison of the expected concentration and the measured electrometer signal is shown in FIG. 21. As expected, the electrometer signal varied linearly with the change in upstream particle concentration. This test provides a validation for the consistency of the electrometer signal with small variation in size distributions.

For size distribution measurements, the flow rate through the instrument was stepped from 0.25 LPM to 1.5 LPM. The classifier and the electrostatic precipitator voltages were set to 500V and 700V respectively. An experimental setup similar to that shown in FIG. 6 is used for this test. The flow rate through the instrument was controlled by an adjustable valve placed downstream of the instrument. The electrometer data was continuously acquired via a RS232 port using a LabView code.

Figure 22:
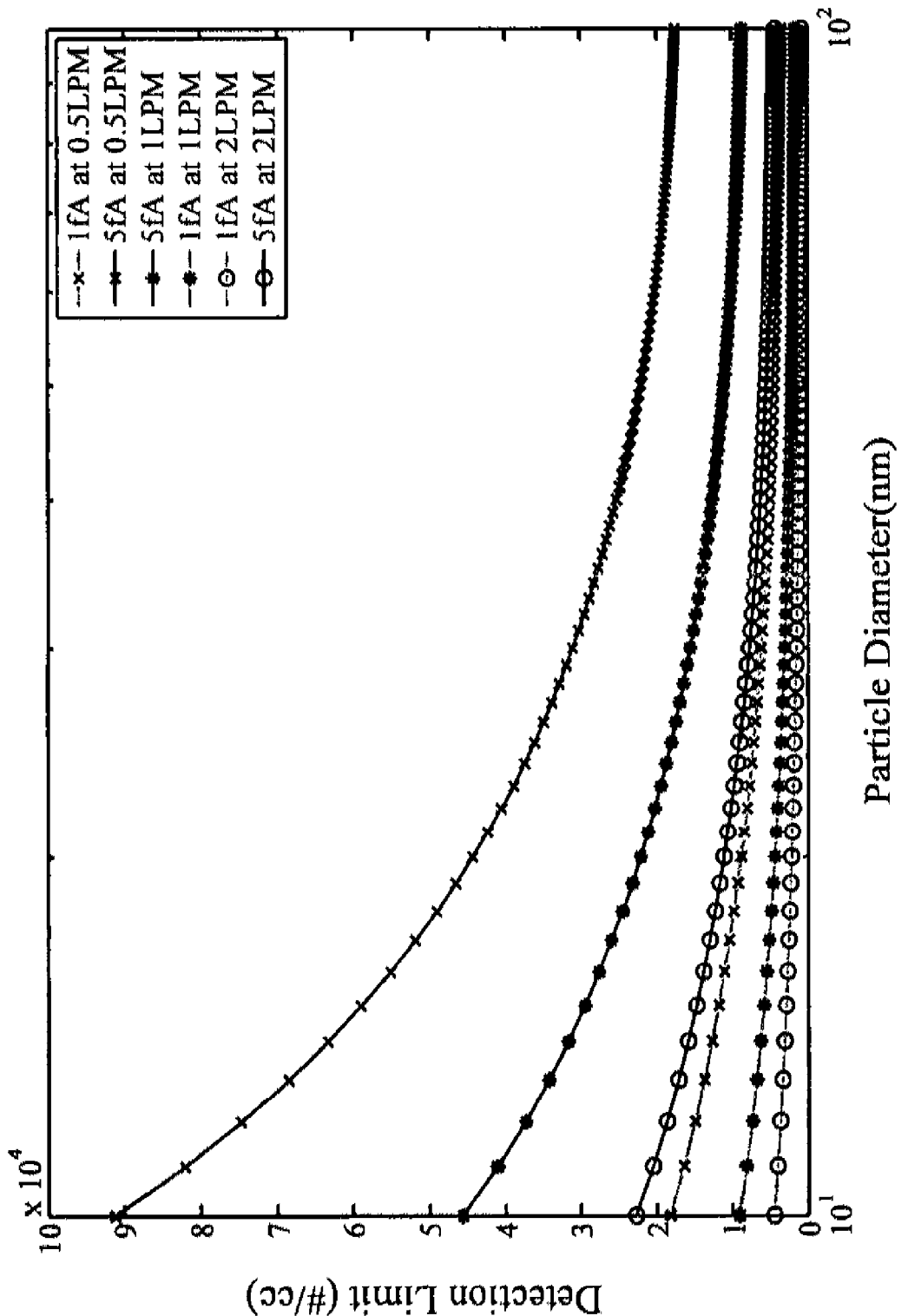
FIG. 22 illustrates the minimum concentration for detection with for electrometer noise levels of 1 and 5 fA and flow rates of 0.5, 1 and 2 LPM.

The theoretical instrument transfer functions were used with first order inversion routine to calculate the size distribution. A large upstream particle concentration was used to reduce the effect of electrometer noise on the signal and the flow rates were chosen to ensure minimal overlapping of transfer functions. This facilitates easy size distribution calculation using first order direct inversion. The size distribution obtained with Miniature Electrical-Mobility Aerosol Spectrometer is compared with the upstream Scanning Mobility Particle Spectrometer measurements (FIG. 22).

The size distribution data for Miniature Electrical-mobility Aerosol Spectrometer compares well with SCANNING MOBILITY PARTICLE SPECTROMETER measurements. The large concentrations used in this test ensured sufficient electrometer signal strengths in the range of 30-400 fA. A more stringent test of the Miniature Electrical-mobility Aerosol Spectrometer performance requires measurements with lower particle concentrations and at higher resolution. Increasing the number of measurement channels results in overlapping of transfer functions and complicating data inversion. For such data sets, advanced data inversion techniques are required and our approach is outlined below.

Data Inversion Methodology:

The electrometer response is related to the upstream size distribution and instrument transfer function as:

$$E_i = Qe \int_0^\infty N(\log D_p) \left( \sum_{n=1}^\infty (nf(n, D_p)\Omega_i(n, D_p)) \right) d\log D_p, \quad (1)$$

where $E_i$ is the electrometer current connected to channel i, N is the particle size distribution entering the instrument, n is the number of elementary charges on the particle, e is the charge on an electron, $f$ is the particle charge distribution, $\Omega_i$ is the Miniature Electrical-mobility Aerosol Spectrometer transfer function, and $D_p$ is the particle diameter. This equation is commonly referred to as the Fredholm integral equation of the first kind and its inversion is an ill-posed problem that is further complicated by overlapping set of transfer functions (See Ranjan and Dhaniyala, 2007, hereby incorporated herein by reference). Data inversion for an ill-posed system of equations is discussed by Talukdar and Swihart (2003), Kandilkar and Ramachandran (1999), Lesnic et al. (1996), and Wolfenbarger and Seinfeld (1990), Busign et al. (1980) and Cooper and Spielman (1976), all hereby incorporated herein by reference.

The ill-posed inversion equation is commonly solved with a regularization technique to obtain a best estimate of the size distribution (Talukdar and Swihart, 2003; Lloyd et al., 1997a; Wolfenbarger and Seinfield, 1990, 1991; Bashurova et al., 1991 and Phillips, 1962) all hereby incoporated herein by reference. A regularization technique balances the accuracy of inversion result with the smoothness of the solution using a regularization parameter. One efficient method to determine the regularization parameter is the L-curve optimization technique (See Hansen and O'Leary, 1993, hereby incorporated herein by reference.) used for inversion of differential mobility analyzer data (See Talukdar and Swihart, 2003; Hansen, 1992, Wolfenbarger and Seinfeld, 1991 and Wahba, 1990), all hereby incoprorated herein by reference.

An inversion routine based on the L-curve regularization technique is developed for size distribution calculation with the Miniature Electrical-mobility Aerosol Spectrometer. The L-curve optimization technique (Hansen and O'Leary, 1993) is used to estimate the optimal value of the regularization parameter. The precise value of regularization parameter is obtained by a maximum curvature approach (Hansen, 1992). A known log normal distribution [$\mu$=70 nm, $\sigma$=1.35], was used to test the performance of the inversion routine. Theoretically estimated kernel functions are convolved with the known size distribution to calculate the expected electrometer signal ($E_i$) in terms of particle concentration. To account for signal errors, we consider two types of noise: a Poisson type counting noise ($E_i^{Pois}$) inherent with the expected particle concentration on the collection electrodes; and a Gaussian spectrum ($E_i \epsilon_i$) with mean zero and standard deviation of ($E_i$) to account for the electrometer noise. For inversion tests, the expected electrometer signal is obtained as (Equation 2):

$$E_i^{noisy} = E_i^{Pois} + E_i \epsilon_i; i=1,N \quad (2)$$

where, $E_i^{noisy}$ is the electrometer current with noise in channel i. To estimate the accuracy of inversion for different starting size distributions, the difference between the inverted and actual distribution is represented as percentage area error, $\Delta_{area}$, calculated as:

$$\Delta_{area} = \left[ \frac{\int_{D_i}^{D_f} |N - N_{inv}| dDp}{\int_{D_i}^{D_f} N dDp} \right] * 100, \quad (3)$$

where $N_{inv}$ is the inverted size distribution. The percentage area error as a function of total particle concentration is shown in FIG. 9. As expected, the area error reduces with increasing total concentration. The knowledge of electrometer detection limit, instrument dimensions and operating conditions determines the error for a selected total concentration.

Field Testing

To test the performance of the instrument under low particle concentrations and in field conditions, the Miniature Electrical-mobility Aerosol Spectrometer was tested at the mobile emissions test facility at the New York State Department of Environmental Conservation (NYSDEC), Albany, N.Y. An experimental setup similar to that shown in FIG. 6 is used. A diesel generator (Genset), with a dilution flow of 1:150 and operating at different load conditions, was used as a source of particles. A bipolar neutralizer ($Kr^{85}$) was used as a particle charger. An electrometer (Keithley source meter; Model 6430) was connected to the $3^{rd}$ collection plate from the electrostatic precipitator channel side. The electrostatic precipitator and classifier plate voltages were set to 200V and 500V respectively. Particles were injected from the $3^{rd}$ electrostatic injection channel. A valve was used downstream of Miniature Electrical-mobility Aerosol Spectrometer to change the flow rate through the instrument. Since the detected electrometer signals were low (0.1-1.5 fA) and in the same order of magnitude as RMS noise of the electrometer (0.1-0.2 fA), the background signals were obtained for all flow rate conditions. The signal due to particle collection was obtained as the difference of the measured and background signals. The theoretical Miniature Electrical-mobility Aerosol Spectrometer transfer function for various flow rates were used to invert the electrometer data using the L-curve inversion routine to obtain particle size distributions for different test cases.

Figure 23:
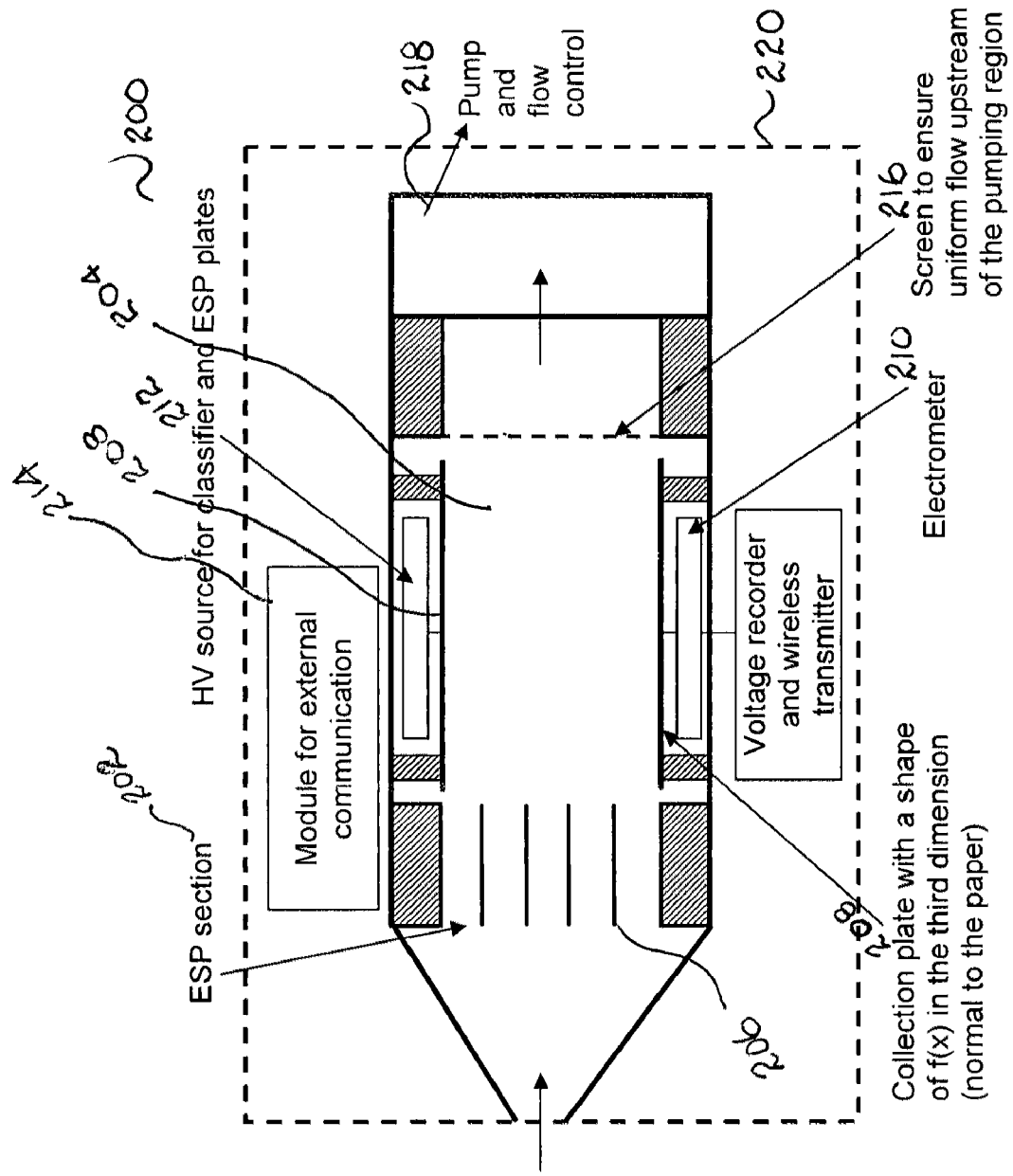
FIG. 23 illustrates a layout of a miniature ultrafine particle sensor.

The size distributions obtained with Miniature Electrical-mobility Aerosol Spectrometer for 0% and 20% load condition is compared with those obtained with a Scanning Mobility Particle Spectrometer system (FIG. 23). The electrometer noise is seen to influence the $zero^{th}$ order inversion, resulting in a noisy size distribution that is largely consistent with the Scanning Mobility Particle Spectrometer measurements. This suggests that the calculated transfer functions accurately represent particle capture characteristics in the Miniature Electrical-mobility Aerosol Spectrometer classifier section. A smoothened distribution obtained using the L-curve optimized inversion routine results in a smooth size distribution that compares closely with the size distribution obtained with the Scanning Mobility Particle Spectrometer. Thus, the inversion algorithm is effective for the overlapping Miniature Electrical-mobility Aerosol Spectrometer transfer functions. The test results suggest that the Miniature Electrical-mobility Aerosol Spectrometer instrument can be field-deployed for measurements such as diesel emission characterization.

Limitations

The minimum particle concentration detected on the collection plates depends on the RMS noise of the electrometer used. Typically, lab-built electrometers have noise in the range of 1-5 fA. The minimum electrometer signal should exceed the noise. The minimum particle concentration required for detection as a function of particle diameter is theoretically calculated and shown in FIG. 23. For these calculations, it is assumed that the particles are charged using a bipolar diffusion charger and that the charge distribution is Boltzmann. For 50 nm particles, more than 2000 $cm^{-3}$ are required at 1 LPM sampling flowrate with an electrometer having 1 fA sensitivity. The minimum particle concentration required for detection is a function of particle diameter, charging technique, and flow rate through the instrument. This result provides a basis to determine the conditions under which Miniature Electrical-mobility Aerosol Spectrometer operation is possible.

Also, to minimize pressure drop through the instrument, no impactor is used upstream of the Miniature Electrical-mobility Aerosol Spectrometer. Thus, for size distributions with significant large particles, multiple charging effects will result in significant error in size distribution measurements.

Conclusions

The theoretical framework for a new electrical-based aerosol sizing instrument called the miniature electrical-mobility aerosol spectrometer (MEAS) has been disclosed. The non-uniform flow and electric fields in the instrument are modeled theoretically and the theoretical results compare well with numerical predictions. A semi-theoretical approach to calculate particle penetration through the electrostatic precipitator section is presented. The theoretical transfer functions obtained considering the electric and flow field non-uniformities and the electrostatic precipitator penetration are seen to closely match the numerically obtained values. The calculations suggest that an optimal injection channel would away from both the collection plates and the classifier HV plate. With moderate flowrates, reasonable particle penetration and resolution are seen to be possible. The Miniature Electrical Aerosol Spectrometer characteristics of compact size, low pressure drop, and a theoretically obtainable transfer function make it very suitable for large scale deployment.

A compact-sized Miniature Electrical-Mobility Aerosol Sepectrometer can be deployed for personal and large scale monitoring under conditions of moderately high particle loading.

Development of a Miniature Ultrafine Particle Sensor

The use of a high-sensitivity electrometer currently limits the capability of using Miniature Electrical-mobility Aerosol Spectrometer for personal sampling or large scale deployment. Such electrometers are expensive $8000) and not portable. A high-sensitivity electrometer is necessary because Miniature Electrical-mobility Aerosol Spectrometer channels only capture particles in a narrow size range and hence often the resulting electrical currents are small (~1 fA). For complete size distribution measurements, an array of electrometers is required, potentially further complicating the instrument and increasing its power requirement and cost. Often, for air quality monitoring and health assessment, a single measure of total ultrafine number is sufficient. For such applications, we disclose a new sensor that is inexpensive, very compact, sensitive, and portable.

For the development of the new miniature ultrafine particle sensor (MUPS), the Miniature Electrical-mobility Aerosol Spectrometer design is modified to include only one collection plate on which all particles in the size range of interest (say 10-100 nm) are captured. The net electrometer signal can then be related to total number of particles in the collected size range. This is simple in concept, but the total ultrafine particle number measurement with this technique is complicated by the size-dependent charging characteristics of the particles. For bipolar diffusion charging, the equilibrium charge fraction is determined as a function of particle size (Wiedensohler, 1988). Larger particles have a greater charged fraction ($f_n$) than smaller particles. Because of this size-dependent charging efficiency, particles with different sizes and same initial total concentration results in very different electrometer signals. Here, a novel approach is outlined to overcome this problem.

FIG. 23 illustrates the layout of a Miniature Ultrafine Particle Sensor 200. As with the Miniature Electrical-mobility Aerosol Spectrometer discussed above, the Miniature Ultrafine Particle Sensor has a rectangular cross-section with two primary regions: the electrostatic precipitator section 202 and the classifier section 204. In the Miniature Ultrafine Particle Sensor 200, the sampled particles first pass through the electrostatic precipitator region 202. This region consists of a set of parallel plates 206 that act as electrostatic precipitators when a potential difference is applied across them. The different plates can be individually maintained at different voltage potentials. The parameters of the electrostatic precipitator section, i.e., number of plates, plate spacing, length, and channel potential difference, are chosen such that charged particles with highest electrical mobility can be electrostatically precipitated through the desired channels. Across one selected electrostatic precipitator channel, called the injection channel, a zero potential difference is maintained to permit the passage of charged particles into a narrow flow region in the classifier section 204. The minimum length of the electrostatic precipitator channel plates is determined by the flow velocity, the available potential difference, and the largest particle mobility to be captured. The smallest spacing between the channels is determined by the breakdown voltage for the operating environmental conditions. The flow through the non-injection electrostatic precipitator channels acts as sheath flow in the classifier section 204.

In the classifier section, a potential difference is maintained to segregate the injected particles by their electrical mobility. This section consists of a classifier plate 208 maintained at high voltage and a single collection plate 208 connected to a electrometer 210. Charged particles condense out of the flow and are trapped on the collection plate 208. The uncharged particles entering through the different electrostatic precipitator channels will exit the classifier section unaffected by the applied electric field. The electrometer 210 connected to the collection plate 208 will output current signals proportional to the number of charged particles trapped on the plate.

In addition, the Miniature Ultrafine Particle Sensor includes: a high voltage source 212 for the classifier 204 and the electrostatic precipitator plates 206; a module for external communication 214; a screen to ensure uniform upstream of the pumping region 216; a pump and flow control device 218; and a case 220.

The electrometer signal due to particles collected on a plate is related to the upstream number concentration (N), the area of collection plate ($A_c^*$), the number of charges on a particle (n), the fraction of particles with n charges ($f_n$) and the size dependent capture efficiency of the collection plate ($\Omega$). The signal (E) can be expressed as:

$$E = \sum_{n=1}^{\infty} neQ \int_0^{\infty} N f_n \Omega A_c^* d\log D_p \quad (14)$$

where e is coulomb charge, Q is the flow rate through the instrument, and Dp is the particle diameter. The parameters N, $f_n$, and $\Omega$ are dependent on particle size. For ultrafine particles, it can be assumed that only a small fraction of particles exist with more than 1 charge; i.e., let $f_n=0$ for n>1. If the area of the collection plate could be chosen such that the parameter ($f_n \Omega A_c^*$) is independent of particle size, then Equation (4) reduces to:

$$E = \kappa \int_0^{\infty} N dD_p = \kappa C \quad (15)$$

Figure 24:
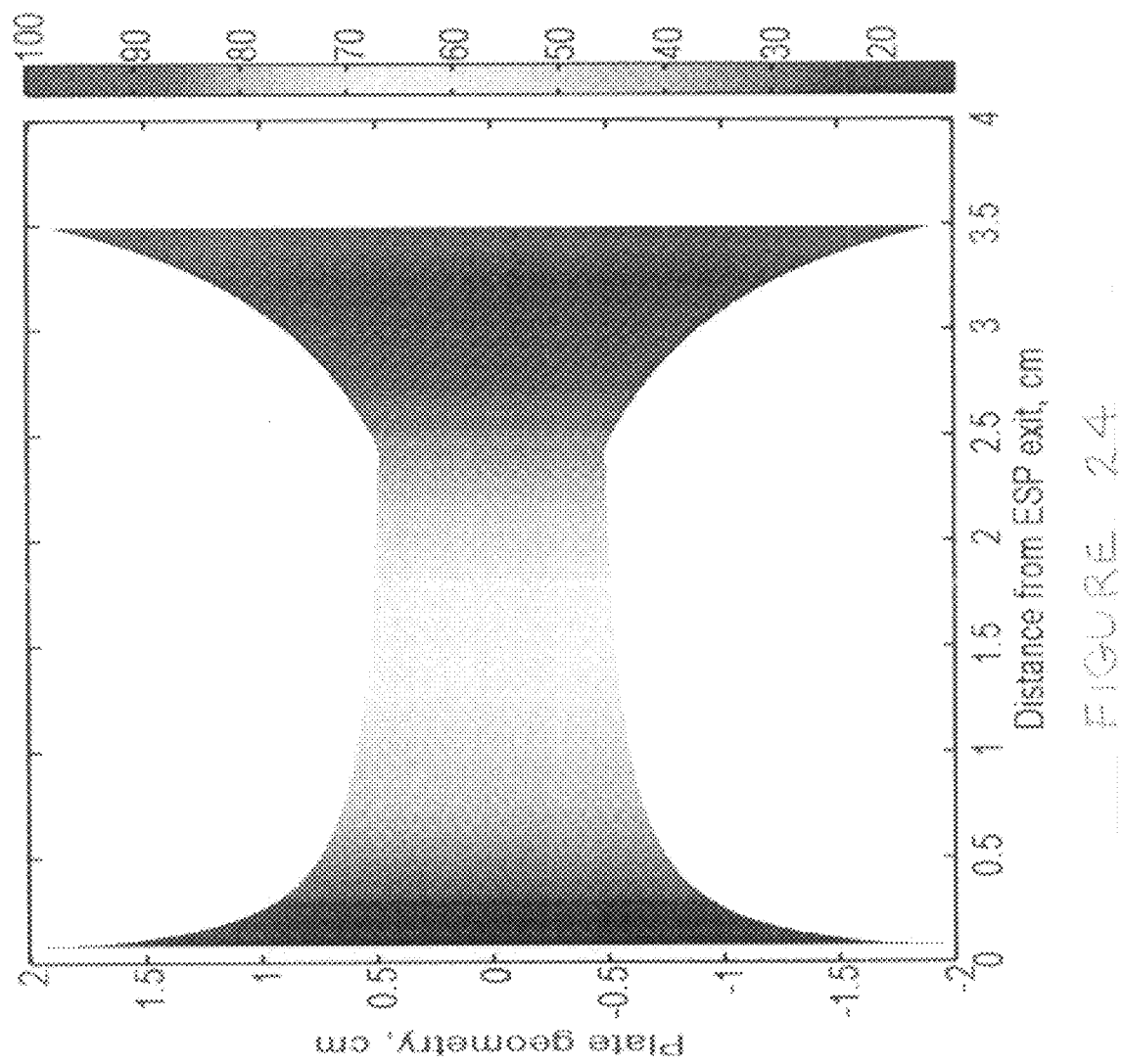
FIG. 24 illustrates collection plate geometry in a miniature ultrafine particle sensor.
Figure 25:
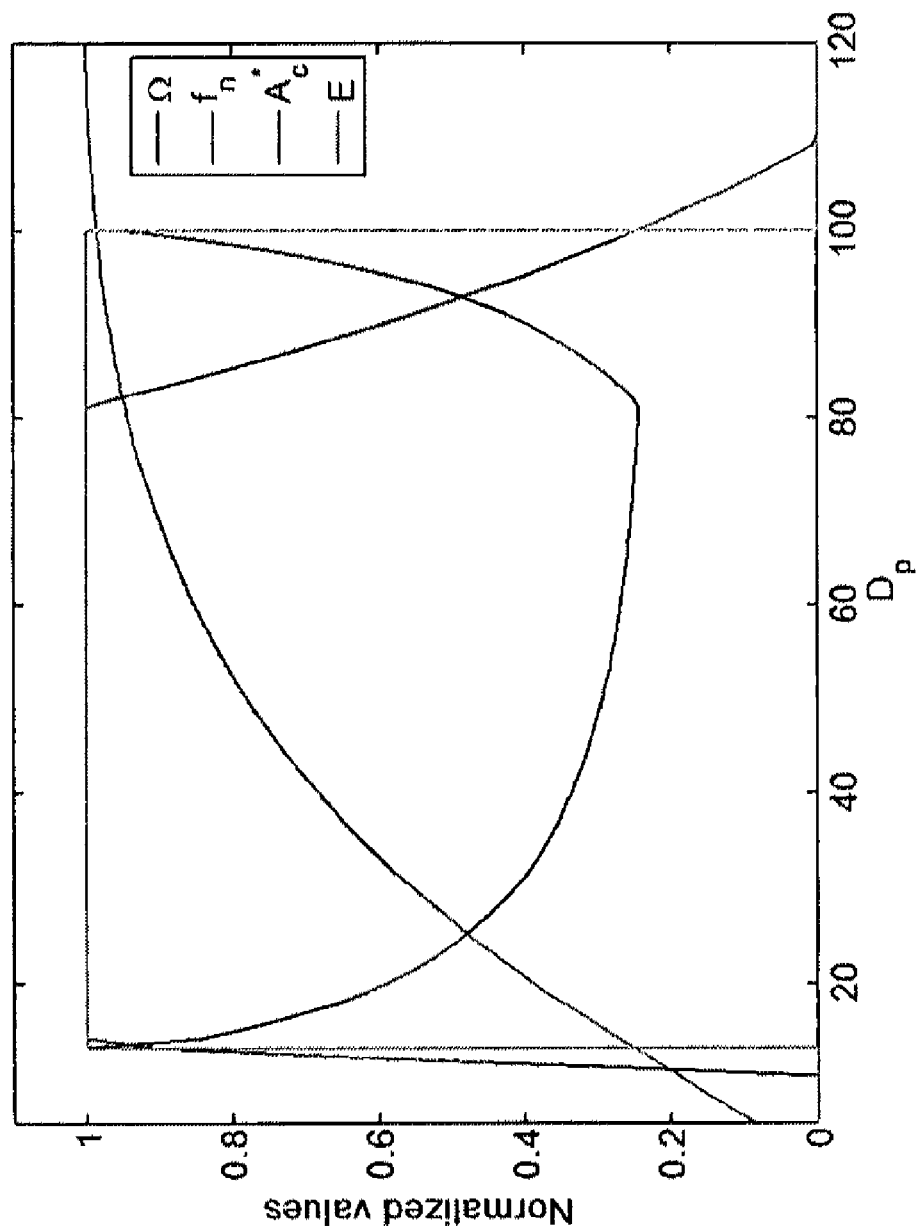
FIG. 25 illustrates normalized values of different parameters as a function of particle diameter.

In Equation (15), C is the total particle concentration in the size range of collection, and K is given as:

$$\kappa = neQf_n \Omega \left( \frac{\int_{x_{Z_p}^{min}}^{x_{Z_p}^{max}} f(x) dx}{w \int_{x_{Z_p}^{min}}^{x_{Z_p}^{max}} dx} \right) \quad (16)$$

where $x^{min}_{Z_p}$ and $x^{max}_{Z_p}$ represent positions along the flow direction (x) between which particles of mobility $Z_p$ are captured and f(x) represents the collection plate width as a function of length along the flow. The total collection plate area is, $$A_c^* = \int_0^L f(x) dx \quad (17)$$

where L is the plate length. Particle capture characteristics on a collection plate of optimized shape [f(x)] would result in an electrometer signal that is only dependent on the total number of particles in the collected size range. In FIG. 24, the shape of the collection plate (top view) obtained from simulations is shown.

For preliminary calculations of f(x), we assumed that particles of a selected mobility (particle size) are captured in a narrow range of x-locations. The change in collection area as a function of x-location can then be determined as:

$$f(x) = \frac{\kappa w}{neQf_n\Omega}(7) \quad (18)$$

Figure 16:
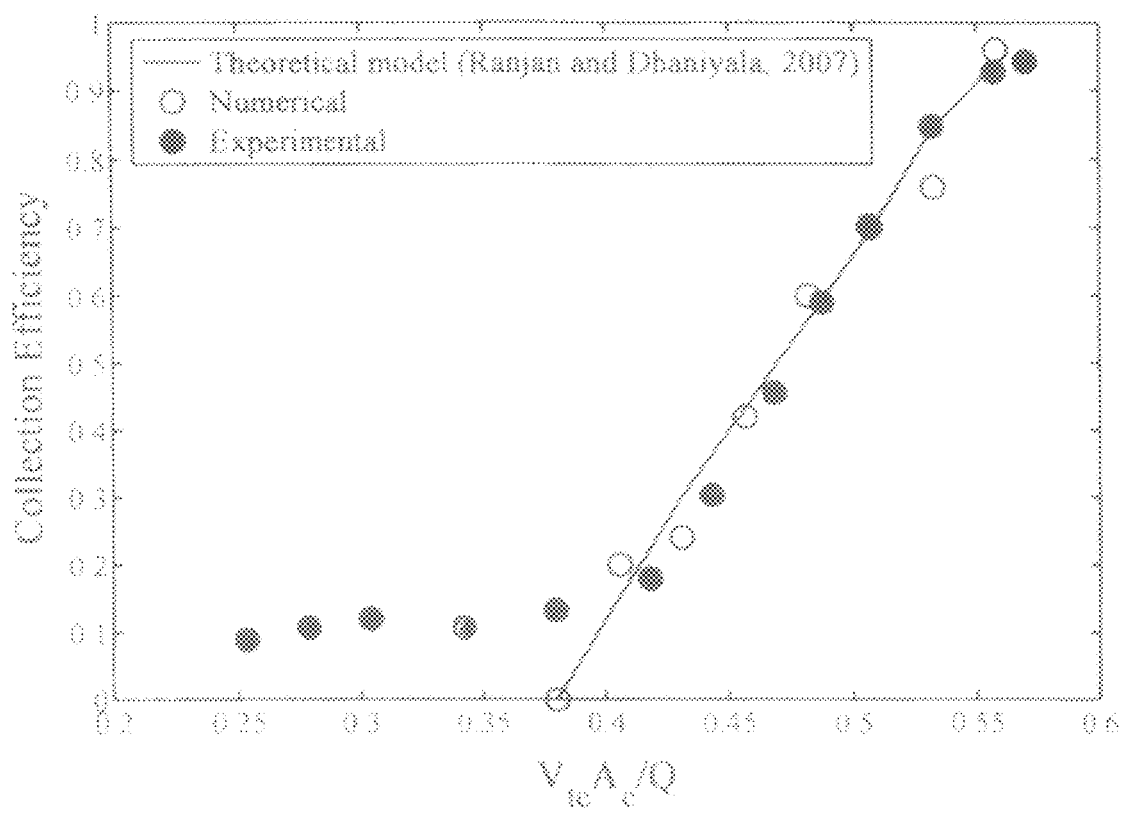
FIG. 16 illustrates a comparison between numerical and experiment collection efficiencies with 350V on the electrostatic precipitator section and with 100 nm particles are passed through the third channel of the electrostatic precipitator section.

Thus, for known transfer function and instrument operating conditions, the collection plate geometry required to obtain a net electrometer signal proportional to total ultrafine number concentration is shown in FIG. 24. For this collection plate geometry, the product of particle fraction captured ($\Omega$), charging fraction ($f_n$), and the collection plate area ($A_c^*$) results in an electrometer response (E) that is particle-size independent (FIG. 16). The net signal from this collection plate will, therefore, be a true measure of the total ultrafine particle number concentration.

The final design of Miniature Ultrafine Particle Sensor requires an accurate calculation of transfer function ($\Omega$) based on non-uniform electric and flow fields that result from the 3D geometry of the electrostatic precipitator and classifier sections. Also, accurate calculation of collection plate geometry [Equation (16)] must be made accounting for the finite particle spatial spreading in the classifier region (as illustrated in FIG. 2). This improved theoretical analysis is used to obtain injection channel and collection plate dimensions that will result in an optimized MUPS design—i.e., the smallest size, low-flowrate instrument that will provide UFP total number concentration measurements with an acceptable accuracy and sensitivity.

A low-power, battery-operated, compact HV source (Emco Inc.) is used for obtain the required electric fields. A battery-operated wireless low voltage recorder/transmitter (Model # OM-CP-RFVOLT101A, Omega Inc) is used for onboard recording of electrometer signals. This device can also wirelessly transmit the data for real-time analysis with an external computer. The layout of the instrument is shown in FIG. 23.

Based on the current electrometer performance characteristics (detection limit of 1 fA, response time of ~2 seconds), we expect to detect ultrafine particle concentrations in the range of $10^2$-$10^3$ cm$^{-3}$ at a rate of 1-10 seconds. There are no upper concentration limits for detection. Improvements in the electrometer design result in a lower particle concentration detection limit and faster collection rate than currently possible.

The foregoing is provided for the purpose of illustrating, explaining and describing embodiments of the present invention. Further modifications and adaptations to these embodiments and methods of achieving an appropriate transfer function will be apparent to those skilled in the art and may be made without departing from the spirit of the invention or the scope of the following claims.

REFERENCES

The following references and those above are hereby incorporated by reference.

Agrawal, J. K., and Sem, G. J. (1980). Continuous Flow, Single-particle-counting condensation Nucleus Counter. Journal of Aerosol Science. 11:343-357

Bashurova, V. S., Koutzenogil, K. P., Pusep, A. Y. and Shokhirev, M. V. (1991). Determination of atmospheric aerosol size distribution function from screen diffusion battery data. Mathematical aspects. Journal of Aerosol Science, 22, 373-388.

Biskos, G., Reavell, K., and Collings, N. (2005). Description and Theoretical Analysis of a Differential Mobility Spectrometer. Aerosol Science and Technology, 39:527-541.

Busigin, A., Vooren W., and Phillips, C. R, (1980). A technique for calculation of aerosol particle size distributions from indirect measurements, Journal of aerosol Science, 11: 359-366.

Buzorius, G., Hämeri, K., Pekkanen, J., Kulmala, M. (1999). Spatial Variation of Aerosol Number Concentration in Helsinki City; Atmos. Environ., 33, 553-565.

Cooper, D. W., and Spielman, L. A., (1976). Data inversion using nonlinear programming with physical constraints: aerosol size distribution measurement by impactors. Atmospheric Environment, 10:723-729.

Hansen, P. C., (1992). Analysis of discrete ill-posed problems by means of the L-curve. SIAM Rec. 34, 561-580.

Hansen, P. C., and O'Leary, D. P. (1993). The Use of the L-Curve in the Regularization of Discrete Ill-Posed Problems, SIAM J. Sci. Comput. 14:1487-1503.

Ibald-Mulli A, Wichmann H E, Kreyling W, Peters A. (2002). Epidemiological evidence on health effects of ultrafine particles. Journal of Aerosol Medicine. 2002 Summer; 15 (2):189-201. Review.

Kandlikar, M., and Ramachandran, G. (1999). Inverse Methods for Analysing Aerosol Spectrometer Measurements: A Critical Review, Journal of Aerosol Science, 30:413-437.

Knutson, E. O., and Whitby, K. T. (1975). Aerosol Classification by Electrical Mobility: Apparatus, Theory, and Applications. J. Aerosol Sci. 6:443-451

Kreyling W G, Semmler M, Erbe F et al. (2002) Translocation of ultrafine insoluble iridium particles from lung epithelium to extrapulmonary organs is size dependent but very low. J Toxicol Env Health Pt A; 65: 1513-30.

Lesnic, D., Elliot, L., and Ingham, D. B. (1996). A Numerical Analysis of the Data Inversion of Particle Sizing Instruments, Journal of Aerosol Science, 27:1063-1082.

Litton C. D., Smith K. R., Edwards R., and Allen T., Combined optical and ionization measurement techniques for inexpensive characterization of micrometer and submicrometer aerosols, Aerosol Science and Technology, 38:1054-1062, 2004

Lloyd, J. J., Taylor, C. J., Lawson, R. S. and Shields, R. A. (1997a). The use of the L-curve method in the inversion of diffusion battery data. Journal of Aerosol Science, 28, 1251-1264.

Matisen, R., Miller, F., Tammet, H., and Salm, J. (1992). Air ion counters and spectrometers Designed in Tartu University, Tartu Ulikooli Toimetised 947:60-67

Mirme, A., 1994. Electric aerosol spectrometry. Ph. D. Thesis. Tartu, 128 pp.

Oberdorster, G., Utell, M. J., (2002). Ultrafine Particles in the Urban Air: To the Respiratory Tract—And Beyond? Environmental Health Perspectives, Vol 110, No 8, August.

Pentane P, Limonene K L, Titanic P, Mirme A, Rosanne J, Pekkanen J: Number concentration and size of particles in urban air: effects on Spiro metric lung function in adult asthmatic subjects. Environ Health Perspex 2001, 109: 319-323.

Phillips, D. L. (1962). A technique for the numerical solution of certain integral equations of the first kind. J. Ass. Comp. Mach. 9, 84-97.

Ranjan, M., Dhaniyala, S., (2007). A New Miniature Electrical Spectrometer: Theory and Design. Journal of Aerosol Science, In press.

Shi, J. P., Evans, D. E., Khan, A. A., and Harrison, R. M. (2001). Sources and concentration of Nanoparticles (<10 nmDiameter) in the Urban Atmosphere, Atmos. Environ. 35(7):1193-1202.

Talukdar, S., and Swihart M., (2003). An Improved Data Inversion Program for Obtaining Aerosol Size Distributions from Scanning Differential Mobility Analyzer Data. Aerosol Science and Technology, 37: 145-161.

Tammet, H., Mirme, A., and Tamm, E. (2002). Electrical Aerosol Spectrometer of Tartu University. Atmospheric Research 62:315-324)

Wahba, G. (1990) Spline Models for Observational Duta. Society for Industrial and Applied Mathematics, Philadelphia.

Wang, S. C., and Flagon, R. C. (1990). Scanning Electrical Mobility Spectrometer. Aerosol Science and Technology. 13:230-240.

Wolfenbarger, J. K., and Seinfeld, J. H. (1990). Inversion of Aerosol Size Distribution Data, Journal of Aerosol Science, 21:227-247.

Wolfenbarger, W. L. and Seinfeld, J. H. (1991) Regularized solutions to the aerosol data inversion problem. SIAM J. Sci. Stat. Comput. 12:342-361.

Zhu, Y., Hinds, W. C., Kim, S., Siestas, C., (2002). Study of ultrafine particles near a major highway with heavy-duty diesel traffic Atmospheric Environment 36 (2002) 4323-4335.

We claim:

1. A miniature electrical-mobility aerosol spectrometer comprising:
a single inlet section that receives particles to be evaluated and is coupled to a multi-channel electrostatic precipitator section;
said electrostatic precipitator section coupled to a classifier section;
said classifier section coupled to an output;
said an outlet is a single flow outlet;
further comprising:
a plurality of upstream plates within said electrostatic precipitator section and a plurality of electrostatic precipitator plates within said precipitator section; and
further comprising:
a high voltage classifier plate; and
one or more collection plates within said classifier section.

2. The spectrometer of claim 1, wherein a transfer function determines an optimum configuration of said electrostatic precipitator section and said classifier section.

3. The spectrometer of claim 2, wherein said transfer function comprises a series of calculations to account for certain non-linear characteristics of an electric field generated within said spectrometer.

4. The spectrometer of claim 3 wherein a closed form of a net flow profile is obtained by combining the individual velocity profiles through said electrostatic channels using a set of Heaviside step functions with a main classifier section velocity profile $$u^E(x, y) = \sum_{i=1}^{Ne+1} \frac{6u_{avg}^E}{(h_u^i - h_l^i)^2}(y - h_l^i) \quad \text{(Equation 1)}$$

$$(h_u^i - y)[U(y - h_l^i) - U(y - h_u^i)][U(-x + p(h_l^i - h_u^{i-1}))];$$

$$u^C(x, y) = \frac{6U_{avg}^C}{H^2}y(H - y)U(x - p(h_l^i - h_u^{i-1})); \quad \text{(Equation 2)}$$

where $u^C(x,y)$ is the velocity in said classifier section away from said electrostatic precipitator-based flow region, and $U_{avg}^C$ is the average velocity through same classifier section, wherein said Equations 1 and 2 are summed to obtain said velocity field [$u^{net}(x,y)$] in said spectrometer classifier section.

5. The spectrometer of claim 4, wherein the velocities obtained from Equations (1) and (2) can be used to calculate the stream function, $\psi(x,y)=\int^{x,y}[u_x dy - u_y dx]$; and where $u_x$ and $U_y$, are the x and y velocity components. The electric flux function, $\phi$ can be calculated as, $\phi(x,y)=\int^{x,y}[E_x dy - E_y dx]$; where Ex, and Ey are the x and y components of the electric field.

6. The spectrometer of claim 5 wherein a particle trajectory in said classifier section is obtained by plotting contours of $\Gamma=\psi+Z_p\phi$=constant where electrical mobility, $Z_p$ is the particle migration velocity in a unit electric field and is given as:

$$Z_p = \frac{neC_c}{3\pi\mu d}$$

where n is an elementary unit of charge, e is the charge on an electron, $C_c$ is a Cunningham Correction factor, $\mu$ is the viscosity of the fluid, and d is the diameter of the particle.

7. The spectrometer of claim 6 wherein a numerical program is used to obtain particle trajectories of a selected diameter or an electrical mobility from said injection channel through said classifier section and further wherein a fraction of contour lines starting at said injection channel that reach a particular collection plate are calculated.

8. The spectrometer of claim 7 wherein said numerical program is repeated for a range of particle diameters to obtain particle capture probability or an instrument transfer function as a function of particle diameter or electrical mobility for a selected collection plate.

9. The spectrometer of claim 8 wherein in order to account for particle transmission efficiency in said electrostatic precipitator section, said electrostatic precipitator section is simulated as a rectangular channel with a boundary condition for the electric potential at an interface of said electrostatic precipitator section and said classifier section are obtained from a numerical solution of integrated classifier and electrostatic precipitator sections and further wherein $\nabla^2 V=0$ is used to obtain a closed form solution of said electric potential distribution inside said channels.

10. The spectrometer of claim 9 wherein a parabolic velocity profile is used to calculate said stream function for the flow in the electrostatic precipitator channel and further wherein said numerical program is repeated for various particle diameters to get a particle penetration through the channel as a function of particle diameter.

11. The spectrometer of claim 10 wherein said diameter dependent particle penetration is accounted for in a collection characteristics curve in said spectrometer to obtain said transfer function for any flow rate and classifier plate voltage.

12. The spectrometer of claim 11 where said transfer function is used with an inversion subroutine to calculate a particle size distribution entering said spectrometer.

13. A miniature ultrafine particle sensor comprising:
a single inlet section that receives the particles to be evaluated and is coupled to electrostatic multichannel precipitator section;
said electrostatic precipitator section coupled to a classifier section;
said classifier section coupled to an output;
an outlet; and
a screen and further comprising:
a pump and flow control;
a high voltage source;
a voltage recorder and wireless transmitter; and
a module for external communication; and further comprising:
a plurality of upstream plates within said electrostatic precipitator section and a plurality of electrostatic precipitator plates within said precipitator section; and further comprising:
a high voltage classifier plate; and
a single collection plate within said classifier section.

14. The sensor of claim 13 wherein appropriately selecting the shape of said collection plate can result in a sensor response that has predetermined particle size dependence.

15. The sensor of claim 14 wherein a transfer function determines an optimum configuration of said electrostatic precipitator section and said classifier section.

16. The sensor of claim 15, wherein said transfer function comprises a series of calculations to account for certain non-linear characteristics of an electric field generated within said sensor.

17. The sensor of claim 16 wherein a closed form of a net flow profile is obtained by combining the individual velocity profiles through said electrostatic channels using a set of Heaviside step functions with a main classifier section velocity profile $$u^E(x, y) = \sum_{i=1}^{Ne+1} \frac{6u_{avg}^E}{(h_u^i - h_l^i)^2}(y - h_l^i) \quad \text{(Equation 1)}$$

$$(h_u^i - y)[U(y - h_l^i) - U(y - h_u^i)][U(-x + p(h_l^i - h_u^{i-1}))];$$

$$u^C(x, y) = \frac{6U_{avg}^C}{H^2}y(H - y)U(x - p(h_l^i - h_u^{i-1})); \quad \text{(Equation 2)}$$

where $U^C(x,y)$ is the velocity in said classifier section away from said electrostatic precipitator-based flow region, and $U^C_{avg}$ is the average velocity through same classifier section, wherein said Equations 1 and 2 are summed to obtain said velocity field [$u^{net}(x,y)$] in said spectrometer classifier section.

18. The sensor of claim 17, wherein the velocities obtained from Equations (1) and (2) can be used to calculate the stream function, $\psi$ as:

$$\psi(x,y) = \int^{x,y} [u_x dy - u_y dx];$$

and where $u_x$ and $u_y$, are the x and y velocity components. The electric flux function, $\phi$ can be calculated as, $$\phi(x,y) = \int^{x,y} [E_x dy - E_y dx],$$

where $E_x$, and $E_y$ are the x and y components of the electric field, calculated from the potential distribution.

19. The sensor of claim 17 wherein a particle trajectory in said classifier section is obtained by plotting contours of $\Gamma = \psi + Z_p \phi =$ constant where electrical mobility, $Z_p$ is the particle migration velocity in a unit electric field and is given as:

$$Z_p = \frac{neC_c}{3\pi\mu d}$$

where n is an elementary unit of charge, e is the charge on an electron, $C_c$ is a Cunningham Correction factor, $\mu$ is the viscosity of the fluid, and d is the diameter of the particle.

20. The sensor of claim 19 wherein a numerical program is used to obtain particle trajectories of a selected diameter or an electrical mobility from said injection channel through said classifier section and further wherein a fraction of contour lines starting at said injection channel that reach a particular collection plate are calculated.

21. The sensor of claim 20 wherein said numerical program is repeated for a range of particle diameters to obtain particle capture probability or an instrument transfer function as a function of particle diameter or electrical mobility for a selected collection plate.

22. The sensor of claim 21 wherein a numerical program is used to obtain equiflow contour paths of particle trajectories of a selected diameter or an electrical mobility from said injection channel through said classifier section and further wherein a fraction of contour lines starting at said injection channel that reach a particular collection plate are calculated.

23. The sensor of claim 22 wherein said numerical program is repeated for a range of particle diameters and a collection probability of said collection plate is obtained as a function of particle diameter or electrical mobility and operating conditions and is known as a transfer function.

24. The sensor of claim 23 wherein in order to account for particle transmission efficiency in said electrostatic precipitator section, said electrostatic precipitator section is simulated as a rectangular channel with a boundary condition for an electric potential at an interface of said electrostatic precipitator and classifier sections obtained from a numerical solution of integrated classifier and electrostatic precipitator sections and further wherein $\nabla^2 V = 0$ is used to obtain a closed form solution of said electric potential distribution inside said channels.

25. The sensor of claim 24 wherein a parabolic velocity profile is used to calculate said stream function for the flow in the electrostatic precipitator channel and further wherein said numerical program is repeated for various particle diameters to get a particle penetration through the channel as a function of particle diameter.

26. The sensor of claim 25 wherein said diameter dependent particle penetration is accounted for in a collection characteristics curve in said sensor to obtain said transfer function for any flow rate and classifier plate voltage.

27. The sensor of claim 26 wherein a final electrometer signal depends on said transfer function, a size dependent particle charging ratio, and said collection ratio as in $$E = \sum_{n=1}^{\infty} neQ \int_0^{\infty} Nf_n \Omega A_c^* d\log D_p \qquad \text{[Equation 6]}$$

where e is coulomb charge, Q is the flow rate through said sensor, $A_c^*$ is the collection area, n is the number of charges, N is the particle size-dependent concentration, is the particle size-dependent instrument transfer function, and Dp is a particle size (diameter).

28. The sensor of claim 27 wherein said collection plate has a width f(x) that varies along the length of said plate, such that the plate area over a narrow length can be calculated as:

$$A_c^* = \left( \int_{x_{Z_p}^{min}}^{x_{Z_p}^{max}} f(x) dx \right)$$

where $x^{min}_{zp}$ and $x^{max}_{zp}$ represent positions along the flow direction between which particles of mobility $Z_p$ are captured and f(x) represents the collection plate width as a function of length along the flow.

29. The sensor of claim 28 wherein an appropriate choice of f(x) results in a sensor response that has a predetermined dependence on particle size. For example, for a net signal proportional to total number concentration over a selected particle size range ($Dp_{min}$ to $Dp_{max}$), f(x) should be selected such that, $$E_{total} = \kappa \int_{Dp_{min}}^{Dp_{max}} N d\log D_p \text{ where } \kappa = eQf_{+1}\Omega \left( \int_{x_{Z_p}^{min}}^{x_{Z_p}^{max}} f(x) dx \right)$$

assuming that charged particle fraction only consists of particles with single charge ($f_{+1}$) wherein as a first order approach to calculate the said collection plate area shape function is to assume that a particle beam width through said electrostatic precipitator injection channel is negligibly small so that f(x) will be constant between $x^{min}_{Z_p}$ and $x^{max}Z_p$ as in $$f(x) = \frac{\kappa w}{neQf_{+1}\Omega} \qquad (9)$$

and wherein a more accurate expression for f(x) can be obtained numerically from the known transfer function ( ), particle charge distribution ($f_n$) and the desired response characteristics.

30. The sensor of claim 29 wherein said collection plate curve with a shape as given by f(x) provides an electrometer signal that has a predetermined dependence on particle size.

31. The sensor of claim 30 wherein, said required response is a signal that is proportional to total ultrafine number concentration, that is of particles smaller than 100 nm.

32. The sensor of claim 30 wherein said signal response is proportional to the number or surface area of ultrafine particles deposited in the lung region.

* * * * *